United States Patent
Tomonari

(10) Patent No.: US 11,339,249 B2
(45) Date of Patent: *May 24, 2022

(54) COMPOUND HAVING FLUORENE SKELETON, AND METHOD FOR MANUFACTURING SAME

(71) Applicant: TEIJIN LIMITED, Osaka (JP)

(72) Inventor: Yasuhiko Tomonari, Osaka (JP)

(73) Assignee: TEIJIN LIMITED, Osaka (JP)

( * ) Notice: Subject to any disclaimer, the term of this patent is extended or adjusted under 35 U.S.C. 154(b) by 14 days.

This patent is subject to a terminal disclaimer.

(21) Appl. No.: 16/965,474

(22) PCT Filed: Jan. 29, 2019

(86) PCT No.: PCT/JP2019/003024
§ 371 (c)(1),
(2) Date: Jul. 28, 2020

(87) PCT Pub. No.: WO2019/151264
PCT Pub. Date: Aug. 8, 2019

(65) Prior Publication Data
US 2020/0354517 A1 Nov. 12, 2020

(30) Foreign Application Priority Data

Jan. 31, 2018 (JP) ............................. JP2018-014773
May 11, 2018 (JP) ............................. JP2018-092229

(51) Int. Cl.
| | | |
|---|---|---|
| C08G 64/06 | (2006.01) | |
| C07C 39/17 | (2006.01) | |
| C07C 43/23 | (2006.01) | |
| C08G 64/30 | (2006.01) | |

(52) U.S. Cl.
CPC .............. *C08G 64/06* (2013.01); *C07C 39/17* (2013.01); *C07C 43/23* (2013.01); *C08G 64/305* (2013.01)

(58) Field of Classification Search
USPC ....... 528/190, 192, 194, 198, 204, 271, 272, 528/279
See application file for complete search history.

(56) References Cited

U.S. PATENT DOCUMENTS

| | | |
|---|---|---|
| 2010/0048855 A1 | 2/2010 | Kato et al. |
| 2015/0179940 A1 | 6/2015 | Mujica-Fernaud et al. |

FOREIGN PATENT DOCUMENTS

| | | |
|---|---|---|
| CN | 102408324 | 4/2012 |
| CN | 104263287 | 1/2015 |
| JP | 2007-23016 | 2/2007 |
| JP | 2009-256342 | 11/2009 |
| JP | 2015-86265 | 5/2015 |
| JP | 2015-530364 | 10/2015 |
| JP | 2016-79405 | 5/2016 |
| JP | 2017-171885 | 9/2017 |
| WO | 2007/142149 | 12/2007 |
| WO | 2009/058396 | 5/2009 |
| WO | 2019/044214 | 3/2019 |

OTHER PUBLICATIONS

International Search Report dated Apr. 16, 2019 in International (PCT) Application No. PCT/JP2019/003024.
Yamada et al., "Synthesis of Fluorenebisphenoxy Derivatives by Acid-sulfur Compound Catalyzed Condensation Reaction", Chemistry Letters, 1998, pp. 1055-1056.
Yuan et al., "Supporting Information for Fluorenone Organic Crystals: Two-Color Luminescence Switching and Reversible Phase Transformations between π-π Stacking-Directed Packing and Hydrogen Bond-Directed Packing", Chemistiy of Materials, 2014, vol. 26, pp. 2467-2477.

*Primary Examiner* — Terressa Boykin
(74) *Attorney, Agent, or Firm* — Wenderoth, Lind & Ponack, L.L.P.

(57) ABSTRACT

Provided are a novel compound having a fluorene skeleton, and a method for manufacturing the same, the compound having a low palladium content or other content of a specific metal or content of a specific compound in a raw material alcohol, and being excellent in hue or various characteristics (optical characteristics, heat resistance, moldability, and other characteristics) as a raw material or in a resin that uses the raw material. This compound is a mixture of compounds having a fluorene skeleton represented by formula (1) (in formula (1), the rings Z being (same or different) aromatic groups, $R^1$ and $R^2$ each independently representing a hydrogen atom, a halogen atom, or a C1-12 hydrocarbon group which may include an aromatic group, $Ar^1$ and $Ar^2$ representing C6-10 aromatic groups which may have a substituent, $L^1$ and $L^2$ representing alkylene groups, j and k each independently representing an integer of 0 or greater, and m and n each independently representing an integer of 0 to 5), the mixture of compounds having a fluorene skeleton being characterized in that the content of elemental palladium therein satisfies formula (2) ((2): 0≤Pd≤50 ppm), and among the mixture of compounds represented by formula (1), compounds comprising the integers m=1-5 and n=0 are included in a range of 0-5%.

30 Claims, No Drawings

COMPOUND HAVING FLUORENE SKELETON, AND METHOD FOR MANUFACTURING SAME

FIELD

The present invention relates to compounds with a fluorene backbone, that are suitable as monomers for forming thermoplastic resins that are to form optical members such as optical lenses or optical films, and that are suitable as starting materials for thermoplastic resins with a high refractive index, low birefringence and excellent balance between heat resistance and moldability, as well as to a method for producing the compounds.

BACKGROUND

In recent years there has been increasing interest in thermoplastic resin materials such as polycarbonates, polyesters and polyester carbonates wherein the starting materials are alcohols with fluorene backbones, among which 9,9-bis(4-(2-hydroxyethoxy)phenyl)fluorene (BPEF) is typical, for use as optical members including optical lenses and optical sheets, because they have excellent optical characteristics, heat resistance and moldability.

PTL 1, for example, discloses a polycarbonate resin wherein the starting material is an alcohol with a BPEF backbone. However, while the refractive index of the polycarbonate resin using such an alcohol is given as 1.64, rapid technological innovation in recent years has led to demand for even better properties. With the aim of achieving a higher refractive index, PTL 2 describes a thermoplastic resin developed using 9,9-bis[4-(2-hydroxyethoxy)-3-phenylphenyl]fluorene (BOPBPEF) as the starting material, but the resin described in this patent document is also in need of improvement in the refractive index. PTL 3 also describes a high-refractive-index resin using 9,9-bis[6-(2-hydroxyethoxy)-2-naphthyl]fluorene (BNEF) as the starting material, but since the birefringence is also high with the higher refractive index, it is associated with significant problems when applied as a transparent material for an optical lens.

Because there is a trade-off between high refractive index and low birefringence, it has been difficult to achieve both properties with conventional polycarbonates and polyester resins.

Incidentally, a method for producing 9,9-bis(4-(2-hydroxyethoxy)phenyl)fluorene (BPEF) has been disclosed, in which sulfuric acid and a thiol are used as catalysts for dehydrating condensation of fluorenone and phenoxyethanol (NPL 1). A method for producing 9,9-bis[6-(2-hydroxyethoxy)-2-naphthyl]fluorene (BNEF) has also been disclosed in which, similar to BPEF, sulfuric acid and a thiol are used as catalysts for dehydrating condensation of fluorenone and 2-naphthoxyethanol (PTL 4). For 9,9-bis[4-(2-hydroxyethoxy)-3-phenylphenyl]fluorene (BOPBPEF) as well, similar to BPEF and BNEF, a method has been disclosed in which sulfuric acid and a thiol are used as catalysts for dehydrating condensation of fluorenone and 2-(2-biphenylyloxy)ethanol (PTL 5), but since all of these methods use large amounts of sulfuric acid, it is necessary to carry out complex purification procedures after reaction, such as neutralization and purification, and this generates a large amount of neutralizing waste water. In addition, inclusion of sulfur components from the catalyst into the product leads to problems such as product coloration, lower stability and lower purity. To obtain a high-purity product such as a resin material for optical use it is also necessary to repeat the purification procedure for removal of the sulfur components, and therefore the method cannot be considered to be industrially advantageous.

CITATION LIST

Patent Literature

[PTL 1] International Patent Publication No. WO2007/142149

[PTL 2] Japanese Unexamined Patent Publication No. 2015-86265

[PTL 3] Japanese Unexamined Patent Publication No. 2017-171885

[PTL 4] Japanese Unexamined Patent Publication No. 2016-79405

[PTL 5] Japanese Unexamined Patent Publication No. 2009-256342

Non Patent Literature

[NPL 1] Chemistry Letters, 1998, p. 1055-1056

SUMMARY

Technical Problem

The method for producing molecularly designed compounds of the following formula (1) according to the invention consists of the two steps outlined below, but even if the alcohol is synthesized using the following formula (6) or (3) and the following formula (7) by the methods described in the aforementioned patent documents, the reaction of step 2 or step (a) is industrially disadvantageous because the reaction either fails to proceed at all, or the reaction rate is slow even if it does proceed. Moreover, when a large amount of catalyst is used in step 1 or step (b) and activated carbon treatment or very similar metal removal treatment is not carried out, then black particles deriving from the palladium catalyst used in the reaction of step 1 or step (b) mixes with the white compound with a fluorene backbone represented by the following formula (1), thus impairing the color tone of the alcohol compound.

According to the invention, therefore, which has been devised upon much research directed toward solving this problem of the prior art, it is an object to provide novel compounds with a fluorene backbone which have a low content of specific metals such as palladium, and a low content of specific compounds, in the alcohol starting material, and that have excellent color tone and properties (such as optical characteristics, heat resistance and moldability) of the starting material and the resin obtained using the starting material, as well as a method for producing them.

Solution to Problem

The present invention, which has been devised as a result of research on solving the aforementioned problems of the prior art, provides compounds with a fluorene backbone that have consistent quality and are superior as polymer starting materials, and a method for producing them. Specifically, the invention relates to the following compounds with a fluorene backbone and method for producing them.

[1] A mixture of compounds with a fluorene backbone represented by the following formula (1):

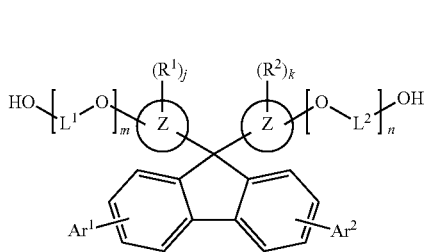
(1)

wherein the rings Z represent the same or different aromatic groups, $R^1$ and $R^2$ each independently represent hydrogen, a halogen atom or a hydrocarbon group of 1 to 12 carbon atoms optionally containing an aromatic group, $Ar^1$ and $Ar^2$ represent an optionally substituted aromatic group of 6 to 10 carbon atoms, $L^1$ and $L^2$ represent alkylene groups, j and k each independently represent an integer of 0 or greater, and m and n each independently represent an integer of 0 to 5, wherein the palladium element content satisfies the following inequality (2):

$$0 \leq Pd \leq 50 \text{ ppm} \qquad (2),$$

and wherein the mixture of compounds represented by formula (1) comprises 0 to 5 wt % of compounds in which in is an integer of 1 to 5 and n=0.

[2] The mixture according to [1] above, wherein each Z is a phenyl group or naphthyl group.

[3] The mixture according to [1] or [2] above, wherein formula (1) is one of the following formulas (1a) to (1d).

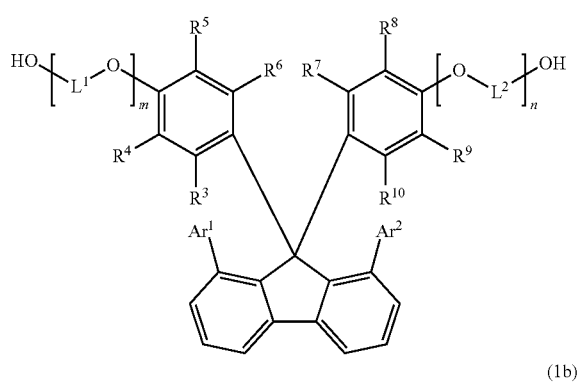
(1a)

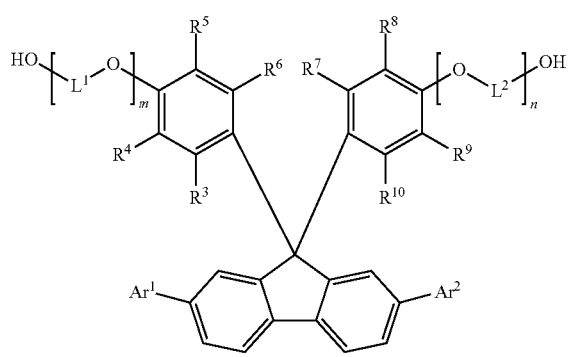
(1b)

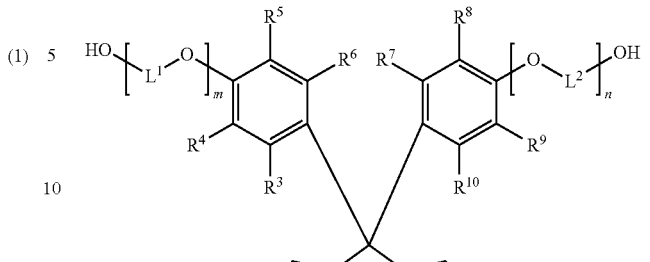
(1c)

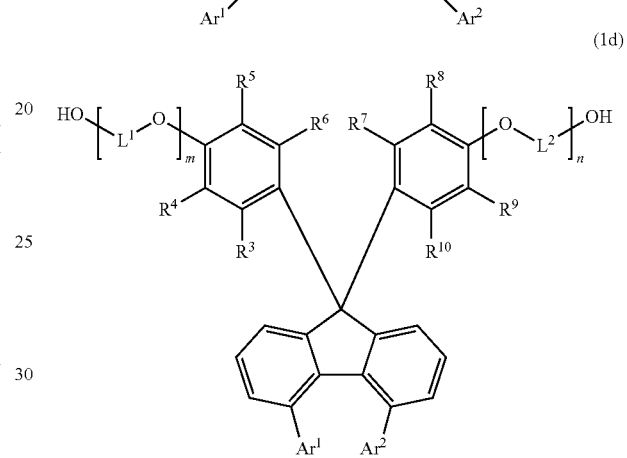
(1d)

wherein $R^3$ to $R^{10}$ each independently represent a hydrogen atom, a halogen atom or a hydrocarbon group of 1 to 12 carbon atoms optionally containing an aromatic group. $Ar^1$ and $Ar^2$, $L^1$ and $L^2$, and m and in and n are the same as in formula (1) above.

[4] The mixture according to [3] above, wherein formula (1) is formula (1b).

[5] The mixture according to any one of [1] to [4] above, wherein $Ar^1$ and $Ar^2$ in formula (1) are phenyl groups or naphthyl groups.

[6] A method for producing a compound with a fluorene backbone represented by formula (1), which includes at least the following step 1 and step 2;

Step 1: A step in which a fluorenone represented by the following formula (3) and a boronic acid represented by the following formula (4) or (5) are reacted in a reaction solvent in the presence of a base and a palladium-based catalyst;

Step 2: A step in which the reaction product (6) produced in step 1 is reacted with an alcohol compound represented by the following formula (7) in a reaction solvent using an acid catalyst;

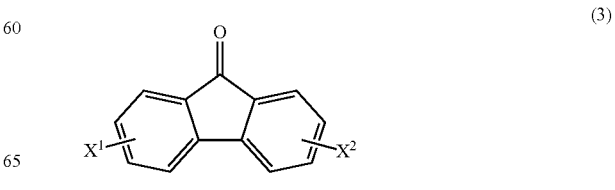
(3)

wherein $X^1$ is a substituent at position 1, position 2, position 3 or position 4, $X^2$ is a substituent at position 5, position 6, position 7 or position 8, and $X^1$ and $X^2$ are both halogen atoms, (4)
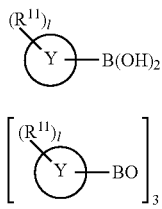

(5)
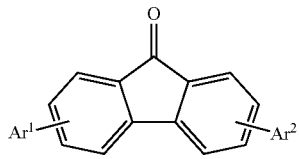

wherein Y is an aromatic group and $R^{11}$ is a hydrogen atom, an alkyl group, an alkenyl group, an alkoxy group or a halogen atom. l is 0, 1 or 2, and when l=2, the two $R^{11}$ groups may be the same or different, (6)
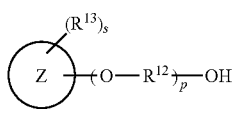

wherein $Ar^1$ and $Ar^2$ are the same as in formula (1), (7)
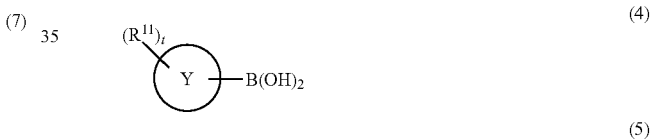

wherein Z is the same as in formula (1), $R^{13}$ is a hydrogen or halogen atom or a hydrocarbon group of 1 to 12 carbon atoms optionally containing an aromatic group, s is independently an integer of 0 or greater, $R^{12}$ represents an alkylene group and p represents an integer of 0 or greater.

[7] A method for producing a compound with a fluorene backbone represented by formula (1), which includes at least the following step (a) and step (b);

Step (a): A step in which a fluorenone represented by the following formula (3) and an alcohol compound represented by the following formula (7) are reacted in a reaction solvent in the presence of an acid catalyst;

Step (b): A step in which the reaction product (8) produced in step (a) is reacted with a boronic acid represented by the following formula (4) or (5) in a reaction solvent in the presence of a base and a palladium-based catalyst;

(3)
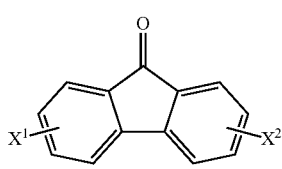

wherein $X^1$ is a substituent at position 1, position 2, position 3 or position 4, $X^2$ is a substituent at position 5, position 6, position 7 or position 8, and $X^1$ and $X^2$ are both halogen atoms, (7)
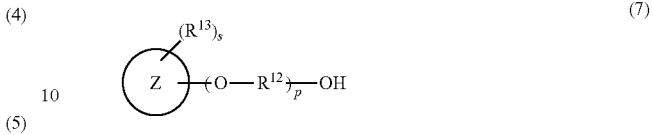

wherein Z is the same as in formula (1), $R^{13}$ is a hydrogen or halogen atom or a hydrocarbon group of 1 to 12 carbon atoms optionally containing an aromatic group, s is independently an integer of 0 or greater, $R^{12}$ represents an alkylene group and p represents an integer of 0 or greater, (8)
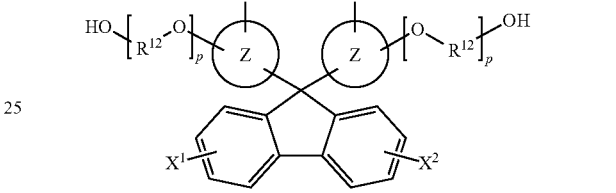

$X^1$ and $X^2$ are the same as in formula (3), Z, $R^{13}$, s, $R^{12}$ and p are the same as in formula (7), (4)
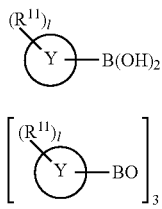

(5)
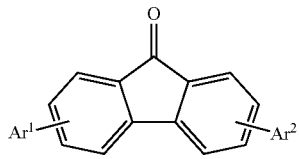

wherein Y is an aromatic group and $R^{11}$ is a hydrogen atom, an alkyl group, an alkenyl group, an alkoxy group or a halogen atom, l is 0, 1 or 2, and when l=2, the two $R^{11}$ groups may be the same or different.

[8] The method fir producing a compound with a fluorene backbone according to [6] or [7] above, wherein the compound represented by formula (3) is 2,7-dibromofluorenone.

[9] The method for producing a compound with a fluorene backbone according to [6] or [7] above, wherein the compound represented by formula (4) is phenylboronic acid, 2-naphthaleneboronic acid or 1-naphthaleneboronic acid.

[10] The method for producing a compound with a fluorene backbone according to [6] or [7] above, wherein the compound represented by formula (5) is phenylboronic anhydride, 2-naphthaleneboronic anhydride or 1-naphthaleneboronic anhydride.

[11] The method for producing a compound with a fluorene backbone according to [6] or [7] above, wherein the compound represented by formula (6) is 2,7-diphenylfluorenone.

[12] The method for producing a compound with a fluorene backbone according to [6] or [7] above, wherein the compound represented by formula (7) is 2-phenoxyethanol.

[13] The method for producing a compound with a fluorene backbone according to [7] above, wherein the compound represented by formula (8) is 9,9-bis(2-hydroxyethoxy)phenyl)-2,7-dibromofluorene.

[14] The method for producing a compound with a fluorene backbone according to [6] or [7] above, wherein the base used in step 1 or step (b) is potassium carbonate and/or sodium carbonate.

[15] The method for producing a compound with a fluorene backbone according to [6] or [7] above, wherein the catalyst used in step 1 or step (b) is tetrakis(triphenylphosphine)palladium and/or palladium acetate.

[16] The method for producing a compound with a fluorene backbone according to [6] or [7] above, wherein the reaction solvent used in step 1 or step (b) is a mixed solvent of toluene and ethanol, or toluene.

[17] The method for producing a compound with a fluorene backbone according to [6] or [7] above, wherein the acid catalyst used in step 2 or step (a) is a heteropolyacid comprising phosphoric acid or silicic acid, and an oxo acid ion of at least one element selected from among vanadium, molybdenum and tungsten.

[18] The method for producing a compound with a fluorene backbone according to [17] above, wherein the heteropolyacid is a heteropolyacid or heteropolyacid anhydride that has previously been subjected to dehydrating treatment.

[19] The method for producing a compound with a fluorene backbone according to [6] or [7] above, wherein the reaction solvent used in step 2 or step (a) is toluene.

[20] A method of using a compound with a fluorene backbone according to [1] above as a starting material for a thermoplastic resin.

Advantageous Effects of Invention

The fluorene compounds of the invention have a low content of specified metals, such as palladium, and a low content of specified compounds, and therefore thermoplastic resins obtained using such fluorene compounds as starting materials have excellent optical characteristics as well as excellent physical properties (heat resistance, color tone and moldability). According to the invention it is also possible to efficiently produce compounds with a fluorene backbone having such excellent properties.

DESCRIPTION OF EMBODIMENTS

The present invention will now be explained in detail, with the understanding that the constituent features described below are merely representative examples of embodiments of the invention and are not meant to limit the content thereof.

The term "Mixture of compounds" as used herein means a composition including or consisting of, in addition to these compounds, impurities that are by-products of production of the compounds and impurities deriving from substances used in the production.

[Mixture of Compounds with Fluorene Backbone]

The mixture of the invention is a mixture of compounds with a fluorene backbone represented by the following formula (1), i.e. compounds with a substitution or addition of two aromatic hydrocarbons having at least one hydroxy group, at position 9 of a fluorene.

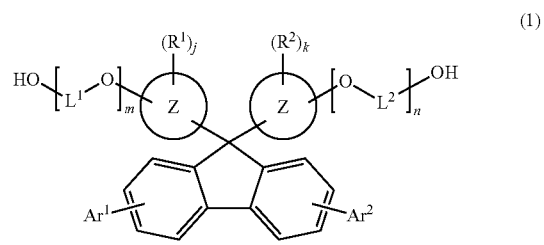

wherein the rings Z represent the same or different aromatic hydrocarbon rings, $R^1$ and $R^2$ each independently represent a hydrogen atom, a halogen atom or a hydrocarbon group of 1 to 12 carbon atoms optionally containing an aromatic group, $Ar^1$ and $Ar^2$ represent optionally substituted aromatic groups of 6 to 10 carbon atoms, $L^1$ and $L^2$ represent alkylene groups, j and k each independently represent an integer of 0 or greater, and m and n each independently represent an integer of 0 to 5.

The aromatic groups represented by rings Z in formula (1) may be benzene rings or fused-polycyclic aromatic hydrocarbons having at least a benzene ring backbone, with preferred examples being fused bi- to tetracyclic hydrocarbon rings such as fused bicyclic hydrocarbons and fused tricyclic hydrocarbons.

A fused bicyclic, hydrocarbon ring is preferably an indene ring or naphthalene ring of 8 to 20 carbon atoms (hereunder also indicated as "$C_{8-20}$"), and more preferably a $C_{10-16}$ fused bicyclic hydrocarbon ring. A fused tricyclic hydrocarbon ring is preferably an anthracene ring or phenanthrene ring.

Benzene ring and naphthalene ring are preferred for the rings Z, with benzene ring being more preferred.

Specific examples of preferred aromatic hydrocarbon rings represented by the rings Z in formula (1) are 1,4-phenylene group, 1,4-naphthalenediyl group and 2,6-naphthalenediyl group, with 1,4-phenylene group being more preferred.

The two rings Z substituted at position 9 of the fluorene ring may be identical or different, and more preferably they are identical rings. The substituents on the rings Z substituting at position 9 of the fluorene backbone are not particularly restricted. When the rings Z are naphthalene, for example, the groups corresponding to the rings Z substituting at position 9 of the fluorene ring may be 1-naphthyl or 2-naphthyl groups.

In formula (1), $R^1$ and $R^2$ each independently represent a hydrogen atom, a halogen atom or a hydrocarbon group optionally containing an aromatic group of 1 to 12 carbon atoms, with a hydrogen atom, a methyl group or a phenyl group being preferred.

Examples of hydrocarbon groups represented by $R^1$ and $R^2$ in formula (1) include alkyl groups, cycloalkyl groups, aryl groups, naphthyl groups and aralkyl groups. Specific preferred examples of alkyl groups include $C_{1-6}$ alkyl groups, $C_{1-4}$ alkyl groups or $C_{1-3}$ alkyl groups such as methyl, ethyl, propyl, isopropyl, butyl and t-butyl groups, with $C_{1-3}$ alkyl groups being more preferred, and methyl and ethyl groups being even more preferred.

Specific preferred examples of cycloalkyl groups include $C_{5-8}$ cycloalkyl groups and $C_{5-6}$ cycloalkyl groups such as cyclopentyl and cyclohexyl groups, with $C_{5-6}$ cycloalkyl groups being preferred.

Specific preferred examples of aryl groups include phenyl and alkylphenyl groups (such as mono- or dimethylphenyl, tolyl, 2-methylphenyl and xylyl groups), with phenyl group being preferred.

Specific preferred examples of aralkyl groups include $C_{6-10}$ aryl-$C_{1-4}$ alkyl groups such as benzyl and phenethyl groups.

Preferred halogen atoms are fluorine, chlorine and bromine.

In formula (1), the substituent numbers j and k for substituents $R^1$ and $R^2$ are not particularly restricted and may be selected as appropriate for the number of fused rings of the fused hydrocarbon, but they are preferably each independently integers of 0 or greater, and more preferably 1 or greater. They are also preferably integers of no greater than 6 and more preferably integers of no greater than 4. The number of substituents j and k in the rings Z may be the same or different, but in most cases they will be the same.

In formula (1), $L^1$ and $L^2$ each independently represent a divalent linking group, which is preferably an alkylene group of 1 to 12 carbon atoms, and more preferably an ethylene group. $L^1$ and $L^2$ will usually be identical alkylene groups on the same ring Z. $L^1$ and $L^2$ may also be the same or different on different rings Z, but normally they will be the same.

The numbers (numbers of moles of addition) of the oxyalkylene groups ($OL^1$) and ($OL^2$) m and n may each be selected within a range of 0 to 5, with the lower limit being preferably 0 or greater and the upper limit being preferably 4 or lower, more preferably 3 or lower and even more preferably 2 or lower. They are preferably 0 or 1, and most preferably 1. The values of in and n may be integers or average values, and they may be the same or different on different rings Z.

In formula (1), $Ar^1$ and $Ar^2$ each independently represent an aromatic group of 6 to 10 carbon atoms, and are preferably phenyl groups or naphthyl groups. The groups $Ar^1$ and $Ar^2$ may be different from each other or identical, but they will usually be identical. The bonding positions of $Ar^1$ and $Ar^2$ are preferably position 1 and position 8, position 2 and position 7, position 3 and position 6 or position 4 and position 5, more preferably position 2 and position 7, position 3 and position 6 or position 4 and position 5, and even more preferably position 2 and position 7, of the fluorene backbone.

Representative examples of diol components represented by formula (1) will now be listed, with the understanding that the starting materials to be used in formula (1) of the invention are not limited to these.

Preferred diphenylfluorene types include 9,9-bis(4-(2-hydroxyethoxy)phenyl)-1,8-diphenylfluorene, 9,9-bis(4-(2-hydroxyethoxy)-3-methylphenyl)-1,8-diphenylfluorene, 9,9-bis(4-(2-hydroxyethoxy)-3-phenylphenyl)-1,8-diphenylfluorene, 9,9-bis(4-(2-hydroxyethoxy)-1-naphthyl)-1,8-diphenylfluorene, 9,9-bis(6-(2-hydroxyethoxy)-2-naphthyl)-1,8-diphenylfluorene, 9,9-bis(4-hydroxyphenyl)-1,8-diphenylfluorene, 9,9-bis(4-hydroxy-3-methylphenyl)-1,8-diphenylfluorene, 9,9-bis(4-hydroxy-3-phenylphenyl)-1,8-diphenylfluorene, 9,9-bis(4-hydroxy-1-naphthyl)-1,8-diphenylfluorene, 9,9-bis(6-hydroxy-2-naphthyl)-1,8-diphenylfluorene, 9,9-bis(4-(2-hydroxyethoxy)phenyl)-2,7-diphenylfluorene, 9,9-bis(4-(2-hydroxyethoxy)-3-methylphenyl)-2,7-diphenylfluorene, 9,9-bis(4-(2-hydroxyethoxy)-3-phenylphenyl)-2,7-diphenylfluorene, 9,9-bis(4-(2-hydroxyethoxy)-1-naphthyl)-2,7-diphenylfluorene, 9,9-bis(6-(2-hydroxyethoxy)-2-naphthyl)-2,7-diphenylfluorene, 9,9-bis(4-hydroxyphenyl)-2,7-diphenylfluorene, 9,9-bis(4-hydroxy-3-methylphenyl)-2,7-diphenylfluorene, 9,9-bis(4-hydroxy-3-phenylphenyl)-2,7-diphenylfluorene, 9,9-bis(4-hydroxy-1-naphthyl)-2,7-diphenylfluorene, 9,9-bis(6-hydroxy-2-naphthyl)-2,7-diphenylfluorene, 9,9-bis(4-(2-hydroxyethoxy)phenyl)-3,6-diphenylfluorene, 9,9-bis(4-(2-hydroxyethoxy)-3-methylphenyl)-3,6-diphenylfluorene, 9,9-bis(4-(2-hydroxyethoxy)-3-phenylphenyl)-3,6-diphenylfluorene, 9,9-bis(4-(2-hydroxyethoxy)-1-naphthyl)-3,6-diphenylfluorene, 9,9-bis(6-(2-hydroxyethoxy)-2-naphthyl)-3,6-diphenylfluorene, 9,9-bis(4-hydroxyphenyl)-3,6-diphenylfluorene, 9,9-bis(4-hydroxy-3-methylphenyl)-3,6-diphenylfluorene, 9,9-bis(4-hydroxy-3-phenylphenyl)-3,6-diphenylfluorene, 9,9-bis(4-hydroxy-1-naphthyl)-3,6-diphenylfluorene, 9,9-bis(6-hydroxy-2-naphthyl)-3,6-diphenylfluorene, 9,9-bis(4-(2-hydroxyethoxy)phenyl)-4,5-diphenylfluorene, 9,9-bis(4-(2-hydroxyethoxy)-3-methylphenyl)-4,5-diphenylfluorene, 9,9-bis(4-(2-hydroxyethoxy)-3-phenylphenyl)-4,5-diphenylfluorene, 9,9-bis(4-(2-hydroxyethoxy)-1-naphthyl)-4,5-diphenylfluorene, 9,9-bis(6-(2-hydroxyethoxy)-2-naphthyl)-4,5-diphenylfluorene, 9,9-bis(4-hydroxyphenyl)-4,5-diphenylfluorene, 9,9-bis(4-hydroxy-3-methylphenyl)-4,5-diphenylfluorene, 9,9-bis(4-hydroxy-3-phenylphenyl)-4,5-diphenylfluorene, 9,9-bis(4-hydroxy-1-naphthyl)-4,5-diphenylfluorene and 9,9-bis(6-hydroxy-2-naphthyl)-4,5-diphenylfluorene.

More preferred are those represented by the following formulas (1-a) to (1-h), specifically the following formula (1-a): 9,9-bis(4-(2-hydroxyethoxy)phenyl)-1,8-diphenylfluorene, the following formula (1-b): 9,9-bis(4-(2-hydroxyethoxy)phenyl)-2,7-diphenylfluorene, the following formula (1-c): 9,9-bis(4-(2-hydroxyethoxy)phenyl)-3,6-diphenylfluorene, the following formula (1-d): 9,9-bis(4-(2-hydroxyethoxy)phenyl)-4,5-diphenylfluorene, the following formula (1-e): 9,9-bis(4-hydroxyphenyl)-1,8-diphenylfluorene, the following formula (1-f): 9,9-bis(4-hydroxyphenyl)-2,7-diphenylfluorene, the following formula (1-g): 9,9-bis(4-hydroxyphenyl)-3,6-diphenylfluorene and the following formula (1-h): 9,9-bis(4-hydroxyphenyl)-4,5-diphenylfluorene, and especially the following formula (1-b): 9,9-bis(4-(2-hydroxyethoxy)phenyl)-2,7-diphenylfluorene and the following formula (1-f): 9,9-bis(4-hydroxyphenyl)-2,7-diphenylfluorene.

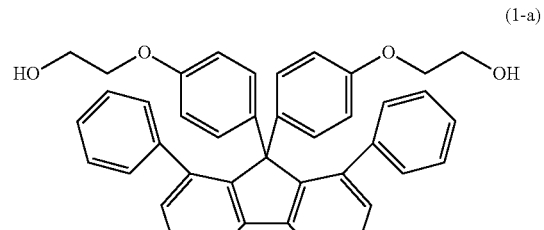

(1-a)

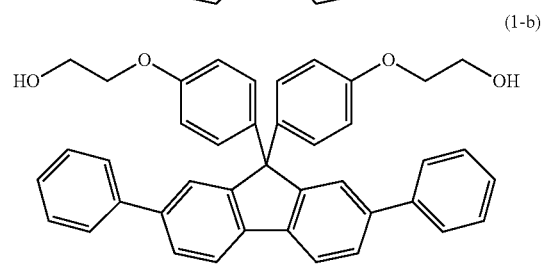

(1-b)

(1-c) 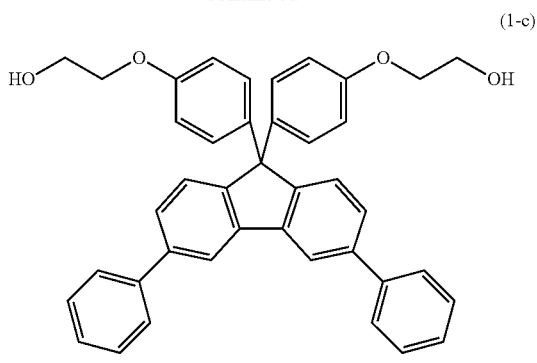

(1-d) 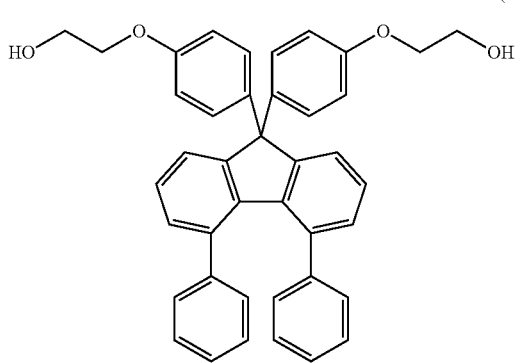

(1-e) 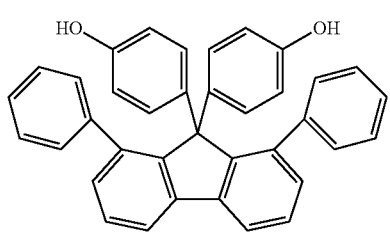

(1-f) 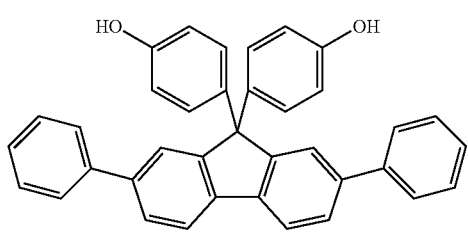

(1-g) 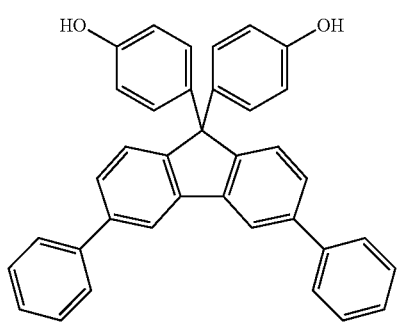

(1-h) 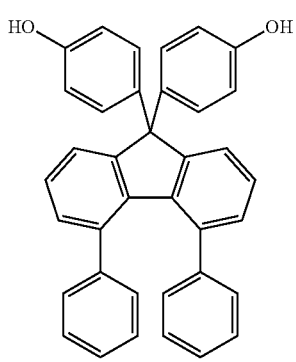

Preferred dinaphthylfluorene types include 9,9-bis(4-(2-hydroxyethoxy)phenyl)-1,8-dinaphthylfluorene, 9,9-bis(4-(2-hydroxyethoxy)-3-methylphenyl)-1,8-dinaphthylfluorene, 9,9-bis(4-(2-hydroxyethoxy)-3-phenylphenyl)-1,8-dinaphthylfluorene, 9,9-bis(4-(2-hydroxyethoxy)-1-naphthyl)-1,8-dinaphthylfluorene, 9,9-bis(6-(2-hydroxyethoxy)-2-naphthyl)-1,8-dinaphthylfluorene, 9,9-bis(4-hydroxyphenyl)-1,8-dinaphthylfluorene, 9,9-bis(4-hydroxy-3-methylphenyl)-1,8-dinaphthylfluorene, 9,9-bis(4-hydroxy-3-phenylphenyl)-1,8-dinaphthylfluorene, 9,9-bis(4-hydroxy-1-naphthyl)-1,8-dinaphthylfluorene, 9,9-bis(6-hydroxy-2-naphthyl)-1,8-dinaphthylfluorene, 9,9-bis(4-(2-hydroxyethoxy)phenyl)-2,7-dinaphthylfluorene, 9,9-bis(4-(2-hydroxyethoxy)-3-methylphenyl)-2,7-dinaphthylfluorene, 9,9-bis(4-(2-hydroxyethoxy)-3-phenylphenyl)-2,7-dinaphthylfluorene, 9,9-bis(4-(2-hydroxyethoxy)-1-naphthyl)-2,7-dinaphthylfluorene, 9,9-bis(6-(2-hydroxyethoxy)-2-naphthyl)-2,7-dinaphthylfluorene, 9,9-bis(4-hydroxyphenyl)-2,7-dinaphthylfluorene, 9,9-bis(4-hydroxy-3-methylphenyl)-2,7-dinaphthylfluorene, 9,9-bis(4-hydroxy-3-phenylphenyl)-2,7-dinaphthylfluorene, 9,9-bis(4-hydroxy-1-naphthyl)-2,7-dinaphthylfluorene, 9,9-bis(6-hydroxy-2-naphthyl)-2,7-dinaphthylfluorene, 9,9-bis(4-(2-hydroxyethoxy)phenyl)-3,6-dinaphthylfluorene, 9,9-bis(4-(2-hydroxyethoxy)-3-methylphenyl)-3,6-dinaphthylfluorene, 9,9-bis(4-(2-hydroxyethoxy)-3-phenylphenyl)-3,6-dinaphthylfluorene, 9,9-bis(4-(2-hydroxyethoxy)-1-naphthyl)-3,6-dinaphthylfluorene, 9,9-bis(6-(2-hydroxyethoxy)-2-naphthyl)-3,6-dinaphthylfluorene, 9,9-bis(4-hydroxyphenyl)-3,6-dinaphthylfluorene, 9,9-bis(4-hydroxy-3-methylphenyl)-3,6-dinaphthylfluorene, 9,9-bis(4-hydroxy-3-phenylphenyl)-3,6-dinaphthylfluorene, 9,9-bis(4-hydroxy-1-naphthyl)-3,6-dinaphthylfluorene, 9,9-bis(6-hydroxy-2-naphthyl)-3,6-dinaphthylfluorene, 9,9-bis(4-(2-hydroxyethoxy)phenyl)-4,5-dinaphthylfluorene, 9,9-bis(4-(2-hydroxyethoxy)-3-methylphenyl)-4,5-dinaphthylfluorene, 9,9-bis(4-(2-hydroxyethoxy)-3-phenylphenyl)-4,5-dinaphthylfluorene, 9,9-bis(4-(2-hydroxyethoxy)-1-naphthyl)-4,5-dinaphthylfluorene, 9,9-bis(6-(2-hydroxyethoxy)-2-naphthyl)-4,5-dinaphthylfluorene, 9,9-bis(4-hydroxyphenyl)-4,5-dinaphthylfluorene, 9,9-bis(4-hydroxy-3-methylphenyl)-4,5-dinaphthylfluorene, 9,9-bis(4-hydroxy-3-phenylphenyl)-4,5-dinaphthylfluorene, 9,9-bis(4-hydroxy-1-naphthyl)-4,5-dinaphthylfluorene and 9,9-bis(6-hydroxy-2-naphthyl)-4,5-dinaphthylfluorene.

More preferred are those represented by the following formulas (2-a) to (2-h), specifically (2-a): 9,9-bis(4-(2-hydroxyethoxy)phenyl)-1,8-dinaphthylfluorene, the following formula (2-b): 9,9-bis(4-(2-hydroxyethoxy)phenyl)-2,7-dinaphthylfluorene, the following formula (2-c): 9,9-bis(4-(2-hydroxyethoxy)phenyl)-3,6-dinaphthylfluorene, the following formula (2-d): 9,9-bis(4-(2-hydroxyethoxy)phenyl)-4,5-dinaphthylfluorene, the following formula (2-e): 9,9-bis(4-hydroxyphenyl)-1,8-dinaphthylfluorene, the following formula (2-f): 9,9-bis(4-hydroxyphenyl)-2,7-dinaphthylfluorene, the following formula (2-g): 9,9-bis(4-hydroxyphenyl)-3,6-dinaphthylfluorene and the following formula (2-h): 9,9-bis(4-hydroxyphenyl)-4,5-dinaphthylfluorene, and especially the following formula (2-b): 9,9-bis(4-(2-hydroxyethoxy)phenyl)-2,7-dinaphthylfluorene and the following formula (2-f): 9,9-bis(4-hydroxyphenyl)-2,7-dinaphthylfluorene.

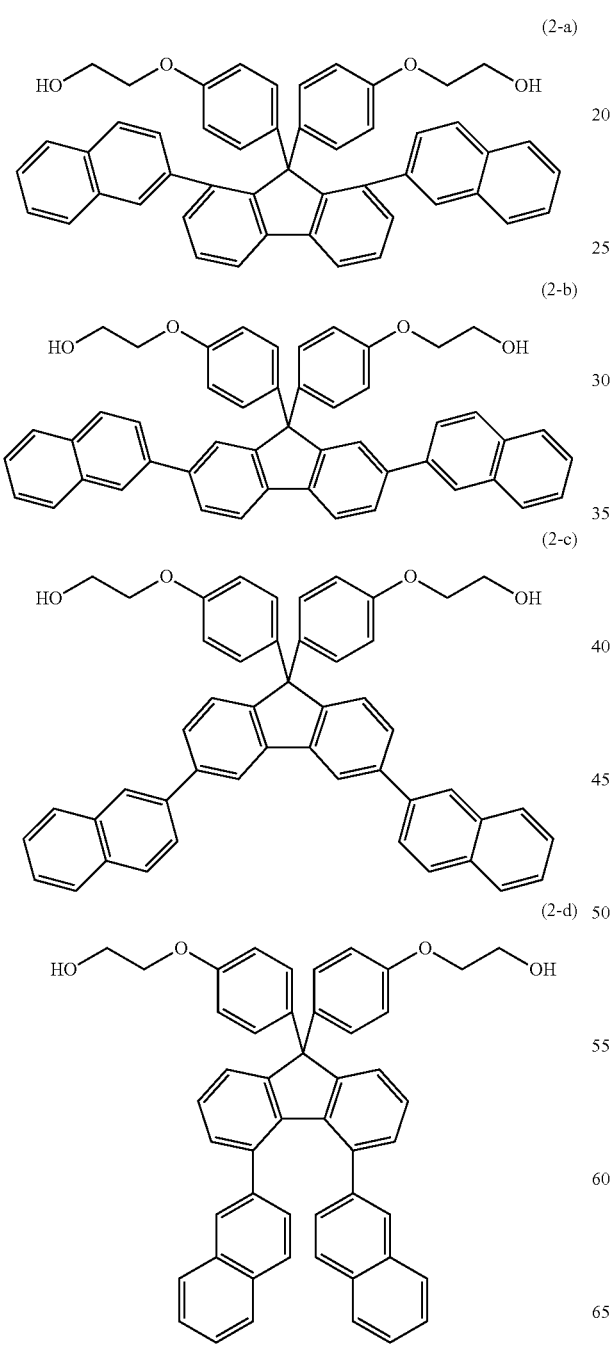

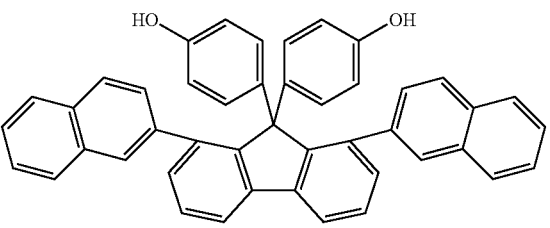

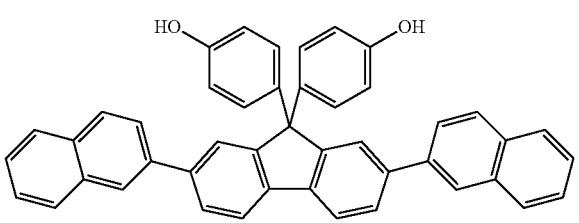

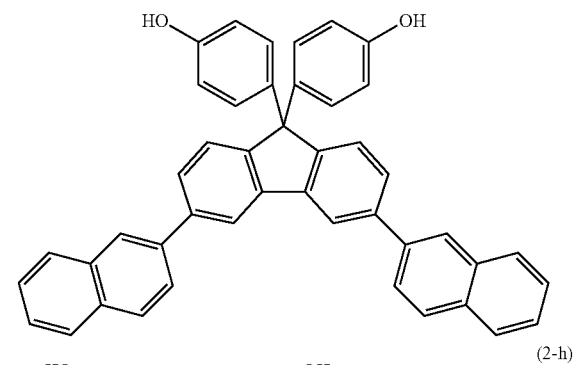

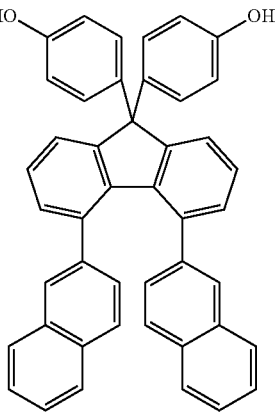

A mixture of compounds with a fluorene backbone according to the invention has a palladium element content satisfying the following inequality (2).

$$0 \leq Pd \leq 50 \text{ ppm} \qquad (2)$$

It preferably satisfies the following inequality (2-1).

$$0 \leq Pd \leq 40 \text{ ppm} \qquad (2\text{-}1)$$

It preferably satisfies the following inequality (2-2).

$$0 \leq Pd \leq 25 \text{ ppm} \qquad (2\text{-}2)$$

It even more preferably satisfies the following inequality (2-3).

$$0 \leq Pd \leq 10 \text{ ppm} \qquad (2\text{-}3)$$

It even yet more preferably satisfies the following inequality (2-4).

$0 \leq Pd \leq 5$ ppm                                            (2-4)

It especially preferably satisfies the following inequality (2-5).

$0 \leq Pd \leq 3$ ppm                                            (2-5)

It most preferably satisfies the following inequality (2-6).

$0 \leq Pd \leq 1$ ppm                                            (2-6)

Exceeding the upper limit of this range is not preferred because it will adversely affect the color tone of resins using the starting alcohol represented by formula (1) or optical members employing them. The lower limit for the palladium element content may be 0.01 ppm or greater, 0.05 ppm or greater or 0.10 ppm or greater.

The mixture of compounds with a fluorene backbone according to the invention includes compounds represented by formula (1) wherein in is an integer of 1 to 5 and n=0, in a range of 0 to 5 wt %, or 0 wt % or greater and less than 5 wt %. For this reason as well, it is in the range of preferably 0 to 3 wt % and more preferably 0 to 1 wt %.

Exceeding the upper limit of this range is not preferred because it can potentially have an adverse effect on productivity (or reactivity) for a resin using the starting alcohol represented by formula (1), and the physical properties (heat resistance, moldability and dimensional stability) of the produced resin.

[Method for Producing Compounds with Fluorene Backbone]

The method for producing compounds with a fluorene backbone represented by formula (1) or their mixture according to the invention is preferably [I] a production method including at least the following step 1 and step 2, or [II] a production method including at least the following step (a) and step (b).

<Production Method [I]>

Production method [I] is largely divided into two steps, allowing production by a first step 1 in which a fluorenone represented by the following formula (3) is reacted with a boronic acid represented by the following formula (4) or (5), and a second step 2 in which the reaction product (6) produced by the first step is reacted with an alcohol compound represented by the following formula (7). With the production method of the invention, the compound with a fluorene backbone or its mixture according to the invention can be produced conveniently and efficiently because reactivity of the boronic acid represented by the following formula (4) or (5) is high and secondary reactions do not occur, while the alcohol represented by the following formula (7) also acts as the reaction solvent and can be easily removed by distillation under reduced pressure.

Step 1

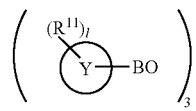
(3)

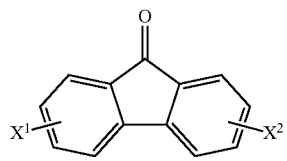
(4)

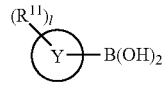

Step 2

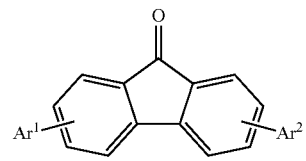
(5)

(6)

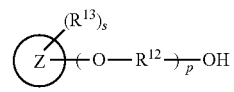
(7)

wherein $X^1$, $X^2$, Y, Z, $Ar^1$, $Ar^2$, $R^{11}$, $R^{12}$, $R^{13}$, 1, p and s are the same as in formulas (3) to (7).

The compounds represented by formula (3) are fluorenone compounds corresponding to the fluorene backbone in formula (1), where $X^1$ is a substituent at position 1, position 2, position 3 or position 4, $X^2$ is a substituent at position 5, position 6, position 7 or position 8, and $X^1$ and $X^2$ are both halogen atoms.

Representative examples of fluorenone compounds represented by formula (3) will now be listed, with the understanding that the starting materials to be used in formula (1) of the invention are not limited to these.

Preferred ones are 1,8-difluorofluorenone, 2,7-difluorofluorenone, 3,6-difluorofluorenone, 4,5-difluorofluorenone, 1,8-dichlorofluorenone, 2,7-dichlorofluorenone, 3,6-dichlorofluorenone, 4,5-dichlorofluorenone, 1,8-diiodofluorenone, 2,7-diiodofluorenone, 3,6-diiodofluorenone, 4,5-diiodofluorenone, 1,8-dibromofluorenone, 2,7-dibromofluorenone, 3,6-dibromofluorenone and 4,5-dibromofluorenone. Preferred among these are 1,8-dibromofluorenone, 2,7-dibromofluorenone, 3,6-dibromofluorenone and 4,5-dibromofluorenone, with 2,7-dibromofluorenone being especially preferred.

They may be used alone or two or more may be combined, with selection as desired depending on the purpose. For the invention, 2,7-dibromofluorenone is preferred.

The purity of the fluorenone represented by formula (3) is not particularly restricted, but usually it is preferred to be 95% or higher, and more preferably 99% or higher. The fluorenone that is used may be a commercial product or a synthesized product. An example of a method for producing dibromofluorenones is described in non-patent literature (Journal of American Chemical Society, 2017, Vol. 139, 11073-11080), and specifically, it is a method of reacting 9-fluorenone and bromine in water.

Ring Y in a compound represented by formula (4) or (5) corresponds to the groups $Ar^1$ and $Ar^2$ in formula (1), and its preferred instances are the same as for $Ar^1$ and $Ar^2$. The preferred instances for group $R^{11}$ in formulas (4) and (5) are the same as the preferred ones for $R^1$ and $R^2$, and the preferred instances for l are the same as the preferred ones for j and k.

The purity of the boronic acid that is used is not particularly restricted, but usually it is preferred to be 95% or higher, and more preferably 99% or higher. The boronic acid that is used may be a commercial product or a synthesized product. An example of a method of producing boronic acids is described in patent literature (Japanese Unexamined Patent Publication No. 2002-47292), and specifically, it is a method of reacting a phenyl Grignard reagent with a boric acid ester dissolved in a non-ether-based aromatic solvent.

Boronic acids to be used for the invention include alkylboronic acids, alkenylboronic acids, arylboronic acids and heteroarylboronic acids represented by formulas (4) and (5) and their anhydrides, with alkylboronic acids including butylboronic acid, cyclohexylboronic acid, cyclopentylboronic acid, 2-ethylboronic acid, 4-ethylboronic acid, hexylboronic acid, isobutylboronic acid, isopropylboronic acid, methylboronic acid, n-octylboronic acid, propylboronic acid, pentylboronic acid, 2-phenylethylboronic acid and their anhydrides, alkenylboronic acids including 1-cyclopentenylboronic acid, ferroceneboronic acid and 1,1'-ferrocenediboronic acid and their anhydrides, arylboronic acids including 2-anthraceneboronic acid, 9-anthraceneboronic acid, benzylboronic acid, 2-biphenylboronic acid, 3-biphenylboronic acid, 4-biphenylboronic acid, 2,3-dimethylphenylboronic acid, 2,4-dimethylphenylboronic acid, 2,5-dimethylphenylboronic acid, 2,6-dimethylphenylboronic acid, 3,4-dimethylphenylboronic acid, 3,5-dimethylphenylboronic acid, 2-ethoxyphenylboronic acid, 3-ethoxyphenylboronic acid, 4-ethoxyphenylboronic acid, 6-methoxy-2-naphthaleneboronic acid, 2-methylphenylboronic acid, 3-methylphenylboronic acid, 4-methylphenylboronic acid, 1-naphthaleneboronic acid, 2-naphthaleneboronic acid, 9-phenanthreneboronic acid, 10-phenyl-9-anthraceneboronic acid, phenylboronic acid, phenylethaneboronic acid, 4-phenyl(naphthalen-1-yl)boronic acid, 3-propoxyphenylboronic acid, 3-iso-propoxyphenylboronic acid, 4-isopropoxyphenylboronic acid, 4-propylphenylboronic acid, 4-iso-propylphenylboronic acid, 10-(naphthalen-1-yl)-9-anthraceneboronic acid and 10-(naphthalen-2-yl)-9-anthraceneboronic acid and their anhydrides, and heteroarylboronic acids including benzofuran-2-boronic acid, dibenzofuran-4-boronic acid, 5-formyl-2-furanboronic acid, 5-formylthiophene-2-boronic acid, furan-2-boronic acid, furan-3-boronic acid, pyridine-3-boronic acid, pyridine-4-boronic acid, quinoline-2-boronic acid, quinoline-3-boronic acid, quinoline-4-boronic acid, quinoline-5-boronic acid, quinoline-6-boronic acid, quinoline-8-boronic acid, iso-quinoline-4-boronic acid, 2-thiopheneboronic acid, 3-thiopheneboronic acid and 5-pyrimidineboronic acid and their anhydrides.

They may be used alone or two or More may be combined, with selection as desired depending on the purpose. Preferred for the invention are phenylboronic acid and 2-naphthaleneboronic acid, and their anhydrides.

The usage ratio of the compound represented by formula (4) to be used as a starting material is about preferably 2 to 5 mol, more preferably 2.05 to 3.0 mol and even more preferably 2.00 to 2.5 mol, with respect to 1 mol of the compound represented by formula (3) (fluorenone halide compound). If the boronic acid is used at less than 2 mol, the yield of product represented by formula (6) may be lowered. If it is greater than 2.5 mol, the reaction rate and yield will be high, but production cost for the compound with a fluorene backbone may also increase.

The usage ratio of the compound represented by formula (5) may be about preferably 1 to 5 mot, more preferably 0.8 to 3 mol and even more preferably 0.7 to 1 mol, with respect to 1 mol of the compound represented by formula (3) (fluorenone halide compound). If the boronic acid is used at less than 0.7 mol, the yield of product represented by formula (6) may be lowered. If it is greater than 1 mol, the reaction rate and the yield will be high, but production cost for the compound with a fluorene backbone may also increase.

The reaction (dehalogenation reaction) between the compounds represented by formula (3) and formula (4) and/or (5) in step 1 may be carried out in a reaction solvent, in the presence of a base and a palladium-based catalyst.

Examples of bases to be used in the reaction of step 1 include inorganic salts, among which are hydroxides such as sodium hydroxide and potassium hydroxide, carbonates such as sodium carbonate ($Na_2CO_3$), potassium carbonate ($K_2CO_3$) and cesium carbonate ($Cs_2CO_3$), acetates such as sodium acetate and potassium acetate and phosphates such as sodium phosphate ($Na_3PO_4$) and potassium phosphate ($K_3PO_4$), triethylamines, pyridine, morpholine, quinoline, piperidine, anilines, and organic salts including ammonium salts such as tetra-n-butylammonium acetate. Carbonates are preferably used among these, with potassium carbonate and/or sodium carbonate being more preferred. Such bases may be used alone, or two or more may be used in combination.

The amount of such bases used in the reaction of step 1 is not particularly restricted, but is preferably added at 1 to 30 equivalents and more preferably 1 to 10 equivalents with respect to 1 mol of the boronic acid.

The palladium-based catalyst to be used in the reaction of step 1 is preferably a palladium compound used in Suzuki coupling, examples of which include tetrakis(triphenylphosphine)palladium, bis(triphenylphosphine)palladium dichloride, palladium acetate, tris(dibenzylideneacetone)dipalladium, bis(dibenzyhdeneacetone)palladium, bis[4-(N,N-dimethylamino)phenyl]di-tert-butylphosphinepalladium dichloride, bis(di-tert-butylprenyl)palladium dichloride and bis(di-tert-crotylphosphine)palladium dichloride. Preferred among these are tetrakis(triphenylphosphine)palladium and/or palladium acetate. Such catalysts may be used alone, or two or more may be used in combination.

The amount of catalyst used in the reaction of step 1 is not particularly restricted, but it is preferably 0.5 to 10 millimole and more preferably 0.6 to 5 millimole, in terms of palladium metal atoms, with respect to 1 mol of the fluorenone compound represented by formula (3). If the amount of palladium catalyst used is less than 0.5 millimoles in terms of palladium metal atoms, it may be difficult fir the reaction to proceed to completion. If the amount of palladium catalyst used is greater than 10 millimole in terms of palladium metal atoms, the reaction will proceed to completion but it will be difficult to limit the palladium element content of the compound with a fluorene backbone to within the range of formula (2), not only potentially impairing the color tone of the thermoplastic resin produced using the alcohol starting material, but also increasing production cost for the compound with a fluorene backbone, in some cases.

Examples of reaction solvents to be used in step 1 include aromatic hydrocarbon-based solvents such as toluene or xylene and alcohols such as methanol, ethanol, isopropyl alcohol and n-butanol, either alone or in combinations. Since an aromatic hydrocarbon-based solvent is a high boiling point solvent, the reaction temperature can be set higher, while using an alcohol is suitable for high affinity with water and satisfactory reactivity. Such solvents may be used alone, or two or more may be used in combination. An aprotic solvent such as N,N-dimethylformamide or N,N-dimethylacetamide or a halobenzene such as o-dichlorobenzene may also be used. Such solvents may be used alone, or two or more may be used in combination. According to the invention, a mixed solvent of toluene and ethanol, or toluene alone, may be used.

The amount of reaction solvent (for the purpose of the invention, a mixed solvent of toluene and ethanol or toluene alone) that is used is not particularly restricted, but the amount of toluene is preferably 0.1 times by weight, more preferably 0.5 to 100 times by weight and even more preferably 1 to 50 times by weight, with respect to the fluorenone represented by formula (3). If the amount of toluene used is less than 0.1 times by weight, the product can potentially precipitate out and create difficulties for stirring. If the amount of toluene used is greater than 100 times by weight, the effect will not be commensurate with the increased amount of usage, while the volumetric efficiency may also be impaired, increasing production cost for the compound with a fluorene backbone. The amount of ethanol used is also not particularly restricted, but it is preferably 0.1 to 50 times by weight and more preferably 1 to 20 times by weight with respect to the fluorenone represented by formula (3). If the amount of ethanol used is less than 0.1 times by weight the reaction rate may be slowed, lowering the yield. If the amount of ethanol used is greater than 50 times by weight, the effect will not be commensurate with the increased amount of usage, as with toluene, while the volumetric efficiency may also be impaired, increasing production cost for the compound with a fluorene backbone.

The reaction temperature will differ depending on the type of starting materials and solvent used, but it is preferably 50 to 150° C., more preferably 60 to 130° C. and even more preferably 70 to 120° C. The reaction can be monitored by analysis means such as liquid chromatography.

Upon completion of the reaction, the reaction mixture will generally contain unreacted fluorenone, unreacted boronic acid, base, catalyst and secondary reaction products, in addition to the product compound represented by formula (6). Therefore, separation and purification may be carried out by separation means using a common method such as filtration, concentration, extraction, crystallization, recrystallization, reprecipitation, activated carbon treatment or highly similar metal removal treatment, or column chromatography, or a combination of these. For example, purification may be carried out by removing the boronic acid by a common method (such as a method of adding an aqueous alkali solution to form a water-soluble complex), and removing the palladium compound by activated carbon treatment or highly similar metal removal treatment, and then adding a recrystallization solvent, cooling for recrystallization, and separating by filtration.

The compound represented by formula (7) ((poly)hydroxyl group-containing arene ring compound) corresponds to a (poly)hydroxyl group-containing arene ring substituted at position 9 in a diarylfluorene derivative represented by formula (6). Specifically, in formula (7), ring Z corresponds to ring Z in formula (1), $R^{12}$ corresponds to $L^1$ and $L^2$, p corresponds to m and n, $R^{13}$ corresponds to $R^1$ and $R^2$ and s corresponds to j and k, and the benzene rings and naphthalene rings mentioned above are examples.

The alkylene group represented by $R^{12}$ is not particularly restricted, and may be an ethylene, propylene, trimethylene, tetramethylene or hexamethylene group, for example. It is preferably an alkylene group of 1 to 6 carbon atoms, and more preferably an alkylene group of 2 to 3 carbon atoms. The substitution position for $R^{12}$ is not particularly restricted. The number of substituents p is 0, 1 or greater, in which case they may be the same or different. It is preferably 0 to 15 and more preferably 0 to 5. When p is 2 or greater, the polyalkoxy group may be composed of identical alkoxy groups or composed of a combination of different alkoxy groups (for example, an ethoxy group and a propyleneoxy group), but it will usually be composed of identical alkoxy groups.

$R^{13}$ represents a hydrogen atom, a halogen atom or a hydrocarbon group optionally containing an aromatic group of 1 to 12 carbon atoms, with a hydrogen atom, a methyl group or a phenyl group being preferred.

Examples of hydrocarbon groups represented by $R^{13}$ include alkyl, cycloalkyl, aryl, naphthyl and aralkyl groups. Specific preferred examples of alkyl groups include $C_{1-6}$ alkyl groups, $C_{1-4}$ alkyl groups or $C_{1-3}$ alkyl groups such as methyl, ethyl, propyl, isopropyl, butyl and t-butyl groups, with $C_{1-3}$ alkyl groups being more preferred, and methyl and ethyl groups being even more preferred. Specific preferred examples of cycloalkyl groups include $C_{5-8}$ cycloalkyl groups and $C_{5-6}$ cycloalkyl groups such as cyclopentyl and cyclohexyl groups, with $C_{5-6}$ cycloalkyl groups being preferred. Specific preferred examples of aryl groups include phenyl and alkylphenyl groups (such as mono- or dimethylphenyl, tolyl, 2-methylphenyl and xylyl groups), with phenyl group being preferred. Specific preferred examples of aralkyl groups include $C_{6-10}$ aryl-$C_{1-4}$ alkyl groups such as benzyl and phenethyl groups. Preferred halogen atoms are fluorine, chlorine and bromine.

The number s of $R^{13}$ substituents may be selected as appropriate depending on the number of fused rings of the fused hydrocarbon and is not particularly restricted, and it may be an integer of preferably 0 or greater and more preferably 1 or greater. It is also preferably an integer of no greater than 6 and more preferably an integer of no greater than 4.

Specific examples of compounds represented by formula (7) where p=0 include alkylphenols such as phenol, 2-methylphenol and 3-methylphenol, dialkylphenols such as 2,3-xylenol, 2,6-xylenol and 3,5-xylenol, alkoxyphenols such as 2-methoxyphenol and 2-ethoxyphenol or phenylphenols such as 2-phenyiphenol and 3-phenylphenol. Examples where p=1 include phenoxyalkyl alcohols such as phenoxyethanol, phenoxypropanol and phenoxybutanol, alkylphenoxyalkyl alcohols such as (2-methyl-phenoxy)ethanol, (3-methyl-phenoxy)ethanol, (3-ethyl-phenoxy)ethanol, (3-butyl-phenoxy)ethanol, (2-methyl-phenoxy)propanol and (3-methyl-phenoxy)propanol, dialkylphenoxyalkyl alcohols such as (2,3-dimethylphenoxy)ethanol, (2,5-dimethylphenoxy)ethanol, (2,6-dimethylphenoxy)ethanol and (2,6-dibutylphenoxy)ethanol, alkoxyphenoxyalkyl alcohols such as (2-methoxyphenoxy)ethanol, cycloalkylphenoxyalkyl alcohols such as (2-cyclohexylphenoxy)ethanol and arylphenoxyalkyl alcohols such as biphenylyloxyethanol. Examples where p is 2 or greater include the polyoxyalkylene phenyl ethers corresponding to these phenoxyalkyl alcohols. Preferred are phenoxy $C_{2-6}$ alkyl alcohols or $C_{1-4}$ alkylphenoxy $C_{2-6}$ alkyl alcohols, with phenoxyethanol being most preferred.

The amount of compound represented by formula (7) used in the reaction of step 2 is not particularly restricted, but from the viewpoint of inhibiting secondary reactions and for economy, it is preferably 2 to 50 mol, more preferably 2.5 to 20 mol and even more preferably 3 to 10 mol, with respect to 1 mol of the fluorenone. These compounds may also be used as the reaction solvent.

The compounds represented by formula (7) may be commercial products or synthesized products. The method for producing a compound represented by formula (7) may be, for example, a method in which the hydroxyl groups of phenols are reacted using ethylene oxide and ethylene carbonate, in the presence of an alkali catalyst.

The purity of the compound represented by formula (7) used as a starting material is not particularly restricted, but usually it is preferred to be 95% or higher, and more preferably 99% or higher.

The reaction of step 2 will usually be carried out in the presence of an acid catalyst. Examples of acid catalysts include sulfuric acid, thiolic acid, montmorillonite and heteropolyacids, among which heteropolyacids are preferred because they have low formation of acid catalyst-derived impurities and can facilitate production of the compound with a fluorene backbone according to the invention.

The term "heteropolyacid" used for heteropolyacids that may be suitably used for the invention generally includes those produced by fusion of two or more different inorganic oxo acids, with there being a variety of possible heteropolyacids obtained by combining a central oxo acid with different types of oxo acids fused around it. A small number of elements that form central oxo acids are referred to as "hetero elements", and elements forming oxo acids that fuse around it are referred to as "poly elements". The poly elements may be of a single type or of multiple different types.

There are no particular restrictions on the hetero element for an oxo acid forming a heteropolyacid, and examples include copper, beryllium, boron, aluminum, carbon, silicon, germanium, tin, titanium, zirconium, cerium, thorium, nitrogen, phosphorus, arsenic, antimony, vanadium, niobium, tantalum, chromium, molybdenum, tungsten, uranium, selenium, tellurium, manganese, iodine, iron, cobalt, nickel, rhodium, osmium, iridium and platinum. Phosphorus (phosphoric acid) and silicon (silicic acid) are preferred. There are also no particular restrictions on the poly elements of oxo acids forming a heteropolyacid, and examples include vanadium, molybdenum, tungsten, niobium and tantalum. They are preferably one or more selected from among vanadium, molybdenum and tungsten.

The heteropolyacid anion used to form the heteropolyacid backbone may be one with any of various different compositions. Examples include $XM_{12}O_{40}$, $XM_{12}O_{42}$, $XM_{18}O_{62}$ and $XM_6O_{24}$. A preferred composition for the heteropolyacid anion is $XM_{12}O_{40}$. In each formula, X is the hetero element and M represents a poly element. Specific examples of heteropolyacids with these compositions include phosphomolybdic acid, phosphotungstic acid, silicomolybdic acid, silicotungstic acid and phosphovanadomolybdic acid.

The heteropolyacid may be a free heteropolyacid, or alternatively a heteropolyacid salt with some or all of the protons replaced with other cations may be used. Therefore, a "heteropolyacid" for the purpose of the invention includes such heteropolyacid salts. Examples of cations that may replace the protons include ammonium, alkali metals and alkaline earth metals.

The heteropolyacid may be an anhydride or a substance containing water of crystallization, but an anhydride is preferred for more rapid reaction and less formation of by-products. With a substance containing water of crystallization, the same effect can be achieved as with an anhydride if dehydrating treatment is carried out beforehand by reduced pressure drying or azeotropic dehydration with a solvent. The heteropolyacid may be in a form supported on a carrier such as active carbon, alumina, silica-alumina or diatomaceous earth. The heteropolyacids may be used alone, or two or more may be used in combination. If necessary, another catalyst other than a heteropolyacid may also be used in a range that does not interfere with the object of the invention.

The amount of heteropolyacid used is not particularly restricted, but in order to obtain a sufficient reaction rate it is preferably at least 0.0001 times by weight, more preferably 0.001 to 30 times by weight and even more preferably 0.01 to 5 times by weight, with respect to the fluorenone.

The method of carrying out the reaction of step 2 is not particularly restricted, but it can generally be carried out by charging the compounds represented by formula (6) and formula (7) together with a heteropolyacid into a reactor, and heating and stirring them in air or under an inert gas atmosphere of nitrogen or argon, in the presence or in the absence of an inert solvent such as toluene or xylene. By carrying out the reaction under dehydrating conditions to remove the water, such as catalyst-containing water and reaction product water, in the reaction system, the reaction can proceed more rapidly than without dehydration, formation of by-products can be reduced, and the target product can be obtained at a higher yield. The dehydration method is not particularly restricted and may be dehydration by addition of a dehydrating agent, dehydration by pressure reduction, or dehydration by azeotropic distillation with a solvent at ordinary pressure or under reduced pressure.

The solvent for azeotropic dehydration is not particularly restricted, and it may be an aromatic hydrocarbon solvent such as toluene or xylene, an aromatic halide hydrocarbon solvent such as chlorobenzene or dichlorobenzene, an aliphatic hydrocarbon solvent such as pentane, hexane or heptane, a halogenated aliphatic hydrocarbon solvent such as dichloromethane or 1,2-dichloroethane, an aliphatic or cyclic ether solvent such as diethyl ether, di-iso-propyl ether, methyl-1-butyl ether, diphenyl ether, tetrahydrofuran or dioxane, an ester solvent such as ethyl acetate or butyl acetate, a nitrile solvent such as acetonitrile, propionitrile, butyronitrile or benzonitrile, or an amide solvent such as N,N-dimethylformamide, N,N-dimethylacetamide or 1-methyl-2-pyrrolidinone. It is preferably an aromatic hydrocarbon solvent or aromatic halide hydrocarbon solvent, more preferably toluene, xylene, chlorobenzene or dichlorobenzene, and even more preferably toluene. The amount used is not particularly restricted, but from the viewpoint of economy it is preferably at least 0.1 times by weight, more preferably 0.5 to 100 times by weight and even more preferably 1 to 20 times by weight, with respect to the fluorenone.

The reaction temperature will differ depending on the type of starting materials and solvent used, but it is preferably 50 to 300° C., more preferably 80 to 250° C. and even more preferably 120 to 180° C. The reaction can be monitored by analysis means such as liquid chromatography.

After the reaction, the obtained reaction mixture may be used directly to precipitate the compound represented by formula (1), but usually the compound represented by formula (1) is precipitated at lower than 50° C. after post-treatment such as rinsing, concentration, dilution and activated carbon treatment. The procedure for precipitating the compound represented by formula (1) from the reaction mixture that has been post-treated as necessary is carried out by raising the temperature of the reaction mixture, combined with a solvent if necessary, to 50° C. or higher and no higher than the boiling point of the solvent (preferably 70 to 110° C.), and then cooling it to lower than 50° C. When crystals of the compound represented by formula (1) precipitate from the reaction mixture at 50° C. or higher, the reaction mixture may be mixed with a diluting solvent in an amount so that crystals do not precipitate out at 50° C. or higher, and the temperature of the obtained mixture may then be raised to 50° C. or higher and no higher than the boiling point of the solvent (preferably 70 to 110° C.), and then cooled to lower than 50° C. The diluting solvent may be any of the examples mentioned above as solvents to be used for the reaction, or an alcohol solvent such as methanol, ethanol, propanol, isopropanol, butanol, t-butanol, isobutanol or pentanol or a carbonate solvent such as dimethyl carbonate or diethyl carbonate, but it is preferably butanol or dimethyl carbonate, and most preferably butanol.

The crystallization procedure may be carried out once or repeated several times. Especially when the acid catalyst in the reaction of step 2 is phosphotungstic acid, using an alcohol such as butanol allows a compound represented by formula (1) satisfying formula (2) to be obtained in a convenient and efficient manner with only a single crystallization procedure.

The precipitated crystals are recovered by filtration, for example. The crystals may be rinsed using the solvent used for the reaction, and they may also be dried. The purity of the purified compound represented by formula (1) that is obtained in this manner is preferably 95% or greater.

The purity of a compound with a fluorene backbone obtained by the production method of the invention may be selected within a wide range of 60 to 100%, but it is preferably 70% or greater, more preferably 80% or greater and even more preferably 90% or greater.

<Production Method [II]>

Production method [II] is largely divided into two steps, allowing production by a first step (a) in which a fluorenone represented by the following formula (3) is reacted with an alcohol compound represented by the following formula (7), and a second step (b) in which the reaction product (8) produced by the first step (a) is reacted with a boronic acid represented by the following formula (4) or (5). With the production method of the invention, the compound with a fluorine backbone or its mixture according to the invention can be produced conveniently and efficiently because the alcohol represented by the following formula (7) also acts as the reaction solvent and can be easily removed by distillation under reduced pressure, while reactivity of the boronic acid represented by the following formula (4) or (5) is high and secondary reactions do not occur.

Step (a)

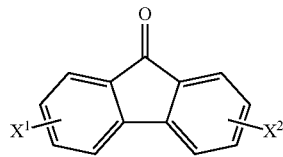

(3)

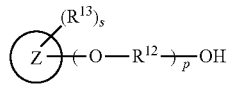

(7)

Step (b)

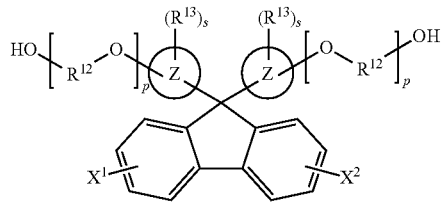

(8)

-continued

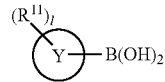

(4)

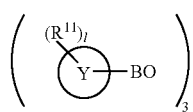

(5)

wherein $X^1$, $X^2$, Y, Z, $R^{11}$, $R^{12}$, $R^{13}$, l, p and s are the same as in formulas (3) to (5) and (7) to (8).

The compound represented by formula (3) may be a compound represented by formula (3) as described above for Production method [I].

The compound represented by formula (7) ((poly)hydroxyl group-containing arene ring compound) corresponds to a (poly)hydroxyl group-containing arene ring substituted at position 9 in a fluorene derivative represented by formula (8). The compound represented by formula (7) is the same as the compound represented by formula (7) described for Production method [I], and its details, amount of use and method of obtainment may be as described for the compound represented by formula (7) for Production method [I].

The reaction of step (a) will usually be carried out in the presence of an acid catalyst. The acid catalyst may be the same one used in step 2 of Production method [I], and the same description applies.

The method for carrying out the reaction of step (a) is the same, other than changing the compound of formula (6) used in step 2 of Production method [I] to a compound of formula (3), and the same description applies.

After the reaction, the reaction mixture may be directly used as starting material for the following step (b), without isolation or purification.

After the reaction, the compound represented by formula (8) may be precipitated from the obtained reaction mixture, and the compound represented by formula (8) may be precipitated at lower than 50° C. after post-treatment such as rinsing, concentration, dilution and activated carbon treatment. The procedure for precipitating the compound represented by formula (8) from the reaction mixture that has been post-treated as necessary is carried out by raising the temperature of the reaction mixture, combined with a solvent if necessary, to 50° C. or higher and no higher than the boiling point of the solvent (preferably 70 to 110° C.), and then cooling it to lower than 50° C. When crystals of the compound represented by formula (1) precipitate from the reaction mixture at 50° C. or higher, the reaction mixture may be mixed with a diluting solvent in an amount so that crystals do not precipitate out at 50° C. or higher, and the temperature of the obtained mixture may then be raised to 50° C. or higher and no higher than the boiling point of the solvent (preferably 70 to 110° C.), and then cooled to lower than 50° C. The diluting solvent may be any of the examples mentioned above as solvents to be used for the reaction, or an alcohol solvent such as methanol, ethanol, propanol, isopropanol, butanol, t-butanol, isobutanol or pentanol or a carbonate solvent such as dimethyl carbonate or diethyl carbonate, but it is preferably ethanol or dimethyl carbonate, and most preferably ethanol.

The crystallization procedure may be carried out once or repeated several times. Especially when the acid catalyst in the reaction of step 2 is phosphotungstic acid, using an alcohol such as ethanol allows a compound represented by formula (8) with a low palladium content to be obtained in a convenient and efficient manner with only a single crystallization procedure.

The precipitated crystals are recovered by filtration, for example. The crystals may be rinsed using the solvent used for the reaction, and they may also be dried. The purity of the purified compound represented by formula (8) that is obtained in this manner is preferably 95% or greater.

Ring Y in the compound represented by formula (4) or (5) is the same as ring Y in the compound represented by formula (4) or (5) in Production method [I], and the same description applies.

In the reaction of step (b), the usage ratio of the compound represented by formula (4) with respect to 1 mol of the fluorene compound represented by formula (8) is the same as the usage ratio of the compound represented by formula (4) with respect to the fluorenone compound represented by formula (3) in step 1 of Production method [I], and the same description applies.

In the reaction of step (b), the usage ratio of the compound represented by formula (5) with respect to 1 mol of the fluorene compound represented by formula (8) is the same as the usage ratio of the compound represented by formula (5) with respect to the fluorenone compound represented by formula (3) in step 1 of Production method [I], and the same description applies.

The reaction (dehalogenation reaction) between the compounds represented by formula (8) and formula (4) and/or (5) in step (b) may be carried out in a reaction solvent, in the presence of a base and a catalyst.

The base used in the reaction of step (b) and the amount used is the same as the base used in the reaction of step 1 of Production method [I] and the amount used, and the same description applies.

The palladium-based catalyst used in the reaction of step (b) is the same as the palladium-based catalyst used in the reaction of step 1 of the Production method [I], and the same description applies.

In the reaction of step (b), the amount of catalyst used with respect to 1 mol of the fluorene compound represented by formula (8) is the same as the amount of catalyst used with respect to the fluorenone compound represented by formula (3) in step 1 of Production method [I], and the same description applies.

The reaction solvent used in step (b) and the amount used is the same as the reaction solvent used in step 1 of Production method [I] and the amount used, and the same description applies.

The reaction temperature in step (b) may be the same as the reaction temperature in step 1 of Production method [I], and the same description applies.

Upon completion of the reaction, the reaction mixture will generally contain unreacted fluorene, unreacted boronic acid, base, catalyst and secondary reaction products, in addition to the product compound represented by formula (1). These may be separated in the same manner as step 1 of Production method [I], and the same description applies.

The purity of a compound with a fluorene backbone obtained by the production method of the invention may be selected within a wide range of 60 to 100%, but it is preferably 70% or greater, more preferably 80% or greater and even more preferably 90% or greater.

[Features and Use of Compounds with Fluorene Backbone]

Since the compounds with a fluorene backbone in the mixture of the invention preferably have a diphenylfluorene backbone or dinaphthylfluorene backbone in combination with an arene ring, they not only exhibit a high refractive index and high heat resistance, but can also reduce birefringence when used as polymers. In order to increase the refractive index in the past, fluorene compounds having aggregated arene rings substituted at position 9 of a fluorene backbone have been used, but this lowers the birefringence with the high refractive index and heat resistance. The compounds with a fluorene backbone in the mixture of the invention, however, have low birefringence while still having a high refractive index, presumably because of the diphenylfluorene backbone. In addition, since the arene ring has one or more hydroxyl groups and multiple hydroxyl groups in the fluorene compound as a whole, the reactivity is high. The mixture of the invention can be used as a starting material (monomer) for various types of resins. For example, it can be used as a monomer for a thermoplastic resin (for example, a polyester resin, polycarbonate resin, polyester carbonate resin or polyurethane resin), or as a polyol component for a thermosetting resin (for example, an epoxy resin, phenol resin, thermosetting polyurethane resin or (meth)acrylate ((meth)acrylic acid ester). When a compound with a fluorene backbone of the invention is to be used as a polyol component, a benzene ring is substituted at position 9 of the fluorene backbone and the fluorene backbone also has a diaryl group, which is presumably why the resulting resin provides the advantage of high levels for both high refractive index and low birefringence.

The mixture of compounds with a fluorene backbone according to the invention can be used to efficiently prepare a derivative in a common solvent.

The melting point of the compounds with a fluorene backbone in the mixture of the invention may be selected in a wide range of 100 to 300° C., preferably 120 to 280° C., more preferably 130 to 260° C., even more preferably 140 to 240° C. and most preferably 150 to 210° C.

EXAMPLES

The present invention will now be explained in greater detail by Examples, with the understanding that the invention is not limited to the Examples so long as its gist is maintained.

The measurements for the Examples were carried out in the following manner.

(1) HPLC Measurement

The compounds obtained in the Examples were measured with the following apparatus and conditions.
Device: Product of Waters Corp.
Column: ACQUITY UPLC@BEH C18, 2.1×150 mm
Eluent (volume): Dimethylformamide:ultrapure water (0.1 wt % trifluoroacetic acid)=70/30

(2) NMR Measurement

The compounds and resins obtained in the Examples were measured with the following apparatus and solvent.
Apparatus: JNM-AL400 (400 MHz) by JEOL Corp.
Solvent: $CDCl_3$ (3) ICP Measurement The compounds obtained in the Examples were measured with the following apparatus.
Device: Agilent Technologies
Apparatus: Agilent5100 ICP-OES (4) Glass Transition Temperature (Tg) Measurement The resins obtained in the Examples were measured with the following apparatus and conditions.
Apparatus: DSC-60A by Shimadzu Corp.
Conditions: Temperature-elevating rate of 20° C./min (5) Pellet b*Value Measurement The resins obtained in the Examples were measured with the following apparatus.
Apparatus: CE-7000A Integrating Sphere Spectrophotometer by X-Rite Co.

(6) Refractive Index (nD), Abbe Number Measurement

The resins obtained in the Examples were measured using the following apparatus and method.
Apparatus: DR-M2 Abbe refractometer by Atago Co.
Method: Resin pellets obtained after polymerization was complete were dissolved in methylene chloride, cast onto a glass dish and dried, and the refractive index (wavelength: 589 nm) and Abbe number (calculated from the refractive index at wavelengths of 486 nm, 589 nm and 656 nm using the following formula) were measured for the prepared film at 25° C.

$$v=(nD-1)/(nF-nC)$$

According to the invention:
nD: refractive index at wavelength of 589 nm,
nC: refractive index at wavelength of 656 nm,
nF: refractive index at wavelength of 486 nm.

Example 1

<Step 1>

After dissolving 25.25 g (74.7 millimole) of 2,7-dibromofluorenone (hereunder also abbreviated as "DBFN") and 19.13 g (156.9 millimole) of phenylboronic acid in 920 mL of a toluene/ethanol mixed solvent (mixing ratio=4/1) and then adding 0.837 g (0.7 millimoles) of tetrakis(triphenylphosphine)palladium and 85 mL of a 2 M potassium carbonate aqueous solution, in a 3 L three-necked flask equipped with a stirrer, cooler and thermometer, the mixture was stirred at 80° C. for 4 hours for reaction. Progression of the reaction was confirmed by HPLC, and the reaction was completed upon confirming a DBFN residue amount of no greater than 0.1 wt %. The obtained reaction mixture was concentrated under reduced pressure to remove the toluene/ethanol, and then a 1 M sodium hydroxide aqueous solution was added to the residue and extraction was performed with chloroform. After palladium catalyst removal treatment of the chloroform layer using active carbon to remove the palladium catalyst remaining in the system, it was concentrated, and when yellow crystals precipitated out the concentration was stopped and recrystallization was carried out directly. The precipitated yellow crystals were filtered out and dried at 85° C. for 24 hours to obtain 20 g of yellow crystals of the target substance, 2,7-diphenylfluorenone (also abbreviated as "DPFN") at a 81% yield.

<Step 2>

After charging 340 g of toluene as a solvent and 2.94 g of 12-tungsto (VI) phosphoric acid n-hydrate ($H_3[PW_{12}O_{40}]\cdot nH_2O$) into a 1 L three-necked flask equipped with a stirrer, cooler, water separator and thermometer, azeotropic dehydration was carried out for 30 minutes with toluene circulation. After cooling the contents, 99.72 g (0.3 mol) of the DPFN synthesized in step 1, 165.80 g (1.2 mol) of 2-phenoxyethanol and 50 g of toluene were added, and the mixture was stirred for 12 hours with toluene circulation while the water generated by the reaction was discharged out of the system. Progression of the reaction was appropriately confirmed by HPLC, and the reaction was completed when the DPFN residue was 0.1 wt % or lower. The obtained reaction mixture was adjusted to 70° C. and rinsed 3 times with 200 g of water. The organic layer was concentrated under reduced pressure to remove the toluene and excess 2-phenoxyethanol. The obtained mixture was dissolved in 500 g of toluene and decolored with active carbon, and since crystals began to precipitate upon concentration of the treatment solution, concentration was stopped and recrystallization was carried out directly. The precipitated white crystals were removed by filtration and dried to obtain 140 g of white crystals of a partially purified product of 9,9-bis(4-(2-hydroxyethoxy)phenyl)-2,7-diphenylfluorene (70% yield, 95.2% purity).

The partially purified product was again recrystallized with a toluene/butanol mixed solvent, to obtain 125 g of white crystals of a purified product of 9,9-bis(4-(2-hydroxyethoxy)phenyl)-2,7-diphenylfluorene (89% yield, 99.0% purity). Measurement of the residual metals by ICP showed Pd at 0.4 ppm. HPLC measurement showed that impurities of compounds represented by formula (1) where m=1 and n=0 were present at 1% in the obtained white crystals.

<Step 3>

After placing 29.51 parts by mass of the 9,9-bis(4-(2-hydroxyethoxy)phenyl)-2,7-diphenylfluorene synthesized in step 2, 21.93 parts by Mass of 9,9-bis[4-(2-hydroxyethoxy)phenyl]fluorene, 21.64 parts by mass of diphenyl carbonate and $42.0 \times 10^{-5}$ parts by mass of sodium hydrogencarbonate in a reaction kiln equipped with a stirrer and distillation device, nitrogen exchange was carried out 3 times, and the jacket was heated to 180° C. to melt the starting materials. After complete dissolution, the pressure was reduced to 20 kPa over a period of 5 minutes while simultaneously increasing the temperature of the jacket to 260° C. at a rate of 60° C./hr, for transesterification reaction. Next, the jacket was kept at 260° C. while reducing the pressure to 0.13 kPa over a period of 50 minutes, and polymerization reaction was carried out under conditions of 260° C., 0.13 kPa until a prescribed torque was reached. Upon completion of the reaction, the produced resin was extracted while being pelletized, to obtain polycarbonate resin pellets. The obtained polycarbonate resin was analyzed by $^1$H NMR, confirming that the 9,9-bis(4-(2-hydroxyethoxy)phenyl)-2,7-diphenylfluorene component had been introduced at 50 mol % with respect to the total monomer component. The refractive index of the obtained polycarbonate resin was 1.664, the Abbe number was 18, the Tg was 161° C. and the pellet b*value was 8.0.

Example 2

A white solid fluorene compound was obtained in the same manner as Example 1, except that the phenylboronic acid in step 1 was changed to phenylboronic anhydride (89% yield, 99.0% purity). Measurement of the residual metals by ICP showed Pd at 0.4 ppm. HPLC measurement showed that impurities of compounds represented by formula (1) where m=1 and n=0 were present at 1% in the obtained white crystals.

Example 3

A white solid fluorene compound was obtained in the same manner as Example 1, except that the base in step 1 was changed to sodium carbonate (89% yield, 99.0% purity). Measurement of the residual metals by ICP showed Pd at 0.4 ppm. HPLC measurement showed that impurities of compounds represented by formula (I) where m=1 and n=0 were present at 1% in the obtained white crystals.

Example 4

A white solid fluorene compound was obtained in the same manner as Example 1, except that the catalyst in step 1 was changed to palladium acetate (89% yield, 99.0% purity). Measurement of the residual metals by ICP showed Pd at 0.4 ppm. HPLC measurement showed that impurities of compounds represented by formula (1) where m=1 and n=0 were present at 1% in the obtained white crystals.

Example 5

A white solid fluorene compound was obtained in the same manner as Example 1, except that the solvent in step 1 was changed to toluene (89% yield, 99.0% purity). Measurement of the residual metals by ICP showed Pd at 0.4 ppm. HPLC measurement showed that impurities of compounds represented by formula (1) where m=1 and n=0 were present at 1% in the obtained white crystals.

Example 6

A white solid fluorene compound was obtained in the same manner as Example 1, except that the catalyst used was the acid catalyst of step 2 that had been dried under reduced pressure beforehand to remove the water of crystallization (89% yield, 99.0% purity). Measurement of the residual metals by ICP showed Pd at 0.4 ppm. HPLC measurement showed that impurities of compounds represented by formula (1) where m=1 and n=0 were present at 1% in the obtained white crystals.

Example 7

A white solid fluorene compound was obtained in the same manner as Example 1, except that the acid catalyst in step 2 was changed to silicotungstic acid n-hydrate ($H_4[SiW_{12}O_{40}] \cdot nH_2O$) (89% yield, 99.0% purity). Measurement of the residual metals by ICP showed Pd at 0.4 ppm. HPLC measurement showed that impurities of compounds represented by formula (1) where m=1 and n=0 were present at 1% in the obtained white crystals.

Example 8

A white solid fluorene compound was obtained in the same manner as Example 6, except for using silicotungstic acid ($H_4[SiW_{12}O_{40}]$) which was the acid catalyst of step 2 that had been dried under reduced pressure beforehand to remove the water of crystallization (89% yield, 99.0% purity). Measurement of the residual metals by ICP showed Pd at 0.4 ppm. HPLC measurement showed that impurities of compounds represented by formula (1) where m=1 and n=0 were present at 1% in the obtained white crystals.

Comparative Example 1

A gray solid fluorene compound was obtained in the same manner as Example 1, except that activated carbon treatment was not carried out in step 1 and step 2 (89% yield, 99.0% purity). Measurement of the residual metals by ICP showed Pd at 70 ppm. HPLC measurement showed that impurities of compounds represented by formula (I) where m=1 and n=0 were present at 1% in the obtained gray crystals.

Polycarbonate resin pellets were obtained in the same manner as Example 1, except that 9,9-bis(4-(2-hydroxyethoxy)phenyl)-2,7-diphenylfluorene synthesized by the method described above was used in step 3. The obtained polycarbonate resin was analyzed by $^1$H NMR, confirming that the 9,9-bis(4-(2-hydroxyethoxy)phenyl)-2,7-diphenylfluorene component had been introduced at 50 mol % with respect to the total monomer component. The refractive index of the obtained polycarbonate resin was 1.664, the Abbe number was 18, the Tg was 161° C. and the pellet b*value was 18.0.

Comparative Example 2

A gray solid fluorene compound was obtained in the same manner as Example 1, except that the amount of tetrakis (triphenylphosphine)palladium used in step 1 was changed to 11.7 g (10 millimole) (89% yield, 99.0% purity). Measurement of the residual metals by ICP showed Pd at 100 ppm. HPLC measurement showed that impurities of compounds represented by formula (1) Where m=1 and n=0 were present at 1% in the obtained white crystals.

Comparative Example 3

Synthesis of a fluorene compound was carried out in the same manner as Example 1, except that the amount of tetrakis(triphenylphosphine)palladium used in step 1 was changed to 0.558 g (0.48 millimole), but although the reaction proceeded, the diphenyl and monophenyl forms were mixed at 95:5 (weight ratio), and it was not possible to obtain the target fluorene compound.

Comparative Example 4

Synthesis of a fluorene compound was carried out in the same manner as Example 1, except that the acid catalyst in step 2 was changed to sulfuric acid and 3-mercaptopropionic acid, but the reaction failed to proceed and the target fluorene compound could not be obtained.

Example 9

<Step (a)>

After charging 150 g of toluene as a solvent and 2.19 g of 12-phosphotungstic (VI) acid n-hydrate ($H_3[PW_{12}O_{40}] \cdot nH_2O$) into a 500 mL flask equipped with a stirrer, cooler and thermometer, azeotropic dehydration was carried out with toluene circulation. After cooling the contents, 33.8 g (0.10 mol) of 2,7-dibromofluorenone (hereunder also abbreviated as DBFN) and 55.3 g (0.40 mol) of 2-phenoxyethanol were added, and the mixture was stirred for 18 hours with toluene circulation while the water generated by the reaction was discharged out of the system. Progression of the reaction was appropriately confirmed by HPLC, and the reaction was completed upon confirming a DBFN residue amount of no greater than 0.1 wt %. The obtained 9,9-bis(2-hydroxyethoxy)phenyl)-2,7-dibromofluorene (hereunder also abbreviated as BPDB) was directly transferred to the reaction of the subsequent step (b) without isolation or purification.

<Step (b)>

After cooling the reaction mixture observed in step (a) to room temperature, 58 mL of a 4 M potassium carbonate aqueous solution, 36.1 g (0.21 mol) of 2-naphthaleneboronic acid and 1.1 g (0.97 millimole) of tetrakis(triphenylphosphinepalladium) were added, and the mixture was stirred at 80° C. for 2 hours for reaction. Progression of the reaction was confirmed by HPLC, and the reaction was completed upon confirming a BPDB residue amount of no greater than 0.1 wt %. The obtained reaction mixture was cooled to room temperature, and after adding ethanol to produce crystallization, the solid was filtered and collected. The collected solid was dissolved in chloroform and rinsed 3 times with hot water, after which the chloroform layer was subjected to decoloration treatment with active carbon and treated for palladium removal, and subsequently concentrated to obtain a partially purified product. The obtained partially purified solid product was recrystallized with toluene to obtain 58 g of white crystals of the target substance, 9,9-bis(4-(2-hydroxyethoxy)phenyl)-2,7-dinaphthylfluorene (80% yield, 98% purity). Measurement of the residual metals by ICP showed Pd at 2.0 ppm. HPLC measurement showed that impurities of compounds represented by formula (1) where m=1 and n=0 were present at 1% in the obtained white crystals.

<Step (c)>

After placing 25.91 parts by mass of the 9,9-bis(4-(2-hydroxyethoxy)phenyl)-2,7-dinaphthylfluorene synthesized in step (b), 16.44 parts by mass of 9,9-bis[4-(2-hydroxyethoxy)phenyl]fluorene, 16.23 parts by mass of diphenyl carbonate and $63.0 \times 10^{-5}$ parts by mass of sodium hydrogencarbonate in a reaction kiln equipped with a stirrer and distillation device, nitrogen exchange was carried out 3 times, and the jacket was heated to 200° C. to melt the starting materials. After complete dissolution, the pressure was reduced to 20 kPa over a period of 5 minutes while simultaneously increasing the temperature of the jacket to 260° C. at a rate of 60° C./hr, for transesterification reaction. Next, the jacket was kept at 260° C. while reducing the pressure to 0.13 kPa over a period of 50 minutes, and polymerization reaction was carried out under conditions of 260° C., 0.13 kPa until a prescribed torque was reached. Upon completion of the reaction, the produced resin was extracted while being pelletized, to obtain polycarbonate resin pellets. The obtained polycarbonate resin was analyzed by $^1$H NMR, confirming that the 9,9-bis(4-(2-hydroxyethoxy)phenyl)-2,7-dinaphthylfluorene component had been introduced at 50 mol % with respect to the total monomer component. The refractive index of the obtained polycarbonate resin was 1.692, the Abbe number was 15, and the Tg was 169° C.

Example 10

A white solid fluorene compound was obtained in the same manner as Example 9, except that the 2-naphthaleneboronic acid in step (b) was changed to 1-naphthaleneboronic acid (80% yield, 98% purity). Measurement of the residual metals by ICP showed Pd at 2.1 ppm.

Example 11

A white solid fluorene compound was obtained in the same manner as Example 9, except that the base in step (b) was changed to sodium carbonate (80% yield, 98% purity). Measurement of the residual metals by ICP showed Pd at 2.0 ppm.

Example 12

A white solid fluorene compound was obtained in the same manner as Example 9, except that the catalyst used was the acid catalyst of step (a) that had been dried under reduced pressure beforehand to remove the water of crystallization (81% yield, 98% purity). Measurement of the residual metals by ICP showed Pd at 2.2 ppm.

Example 13

A white solid fluorene compound was obtained in the same manner as Example 9, except that the acid catalyst in step (a) was changed to silicotungstic acid n-hydrate ($H_4[SiW_{12}O_{40}] \cdot nH_2O$) (79% yield, 98% purity). Measurement of the residual metals by ICP showed Pd at 2.5 ppm.

Example 14

A white solid fluorene compound was obtained in the same manner as Example 9, except that the catalyst used was the acid catalyst of step (a) that had been dried under reduced pressure beforehand to remove the water of crystallization (78% yield, 98% purity). Measurement of the residual metals by ICP showed Pd at 2.2 ppm.

Comparative Example 5

A brown solid fluorene compound was obtained in the same manner as Example 9, except that activated carbon treatment was not carried out in step (b) (79% yield, 97% purity). Measurement of the residual metals by ICP showed Pd at 50.1 ppm.

Polycarbonate resin pellets were obtained in the same manner as Example 1, except that 9,9-bis(4-(2-hydroxyethoxy)phenyl)-2,7-dinaphthylfluorene synthesized by the method described above was used in step (c). The obtained polycarbonate resin was analyzed by $^1$H NMR, confirming that the 9,9-bis(4-(2-hydroxyethoxy)phenyl)-2,7-dinaphthylfluorene component had been introduced at 50 mol % with respect to the total monomer component. The refractive index of the obtained polycarbonate resin was 1.692, the Abbe number was 15, and the Tg was 169° C. The color tone of the polycarbonate resin pellets obtained in Comparative Example 5 was a more intensely yellow color than the color tone of the polycarbonate resin pellets obtained in Example 9.

Comparative Example 6

A brown solid fluorene compound was obtained in the same manner as Example 9, except that the amount of tetrakis(triphenylphosphine)palladium used in step (b) was changed to 11.6 g (10 millimole) (80% yield, 98% purity). Measurement of the residual metals by ICP showed Pd at 120 ppm.

Comparative Example 7

Synthesis of a fluorene compound was carried out in the same manner as Example 9, except that the amount of tetrakis(triphenylphosphine)palladium used in step (b) was changed to 0.56 g (0.48 millimole), but although the reaction proceeded, the dinaphthyl and mononaphthyl forms were mixed at 90:10 (weight ratio) and it was not possible to obtain the target fluorene compound.

Comparative Example 8

Synthesis of a fluorene compound was carried out in the same manner as Example 9, except that the acid catalyst in step (a) was changed to sulfuric acid and 3-mercaptopropionic acid, but the reaction failed to proceed and the target fluorene compound could not be obtained.

INDUSTRIAL APPLICABILITY

With the compounds with a fluorene backbone according to the invention and the method for producing them, it is possible to efficiently produce resin starting materials (monomers) having excellent properties including high refractive index, heat resistance and low birefringence, and the compounds can be suitably used as reaction components for resin starting materials (monomers) and their derivatives.

The compounds with a fluorene backbone or their derivatives according to the invention, and resins using the novel compounds with a fluorene backbone as starting materials (monomers) can be used in optical members such as films, lenses, prisms, optical disks, transparent conductive panels, optical cards, sheets, optical fibers, optical films, optical filters and hard coat films, and in particular they are highly useful for lenses.

The invention claimed is:

1. A mixture of compounds with a fluorene backbone represented by the following formula (1):

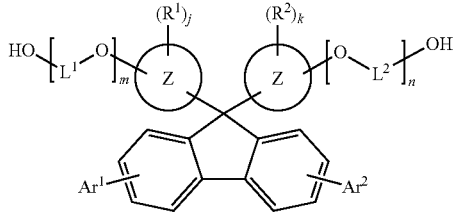

(1)

wherein the rings Z represent the same or different aromatic groups, $R^1$ and $R^2$ each independently represent hydrogen, a halogen atom or a hydrocarbon group of 1 to 12 carbon atoms optionally containing an aromatic group, $Ar^1$ and $Ar^2$ represent an optionally substituted aromatic group of 6 to 10 carbon atoms, $L^1$ and $L^2$ represent alkylene groups, j and k each independently represent an integer of 0 or greater, and m and n each independently represent an integer of 0 to 5, wherein the palladium element content satisfies the following inequality (2):

0≤Pd≤50 ppm                    (2), and wherein the mixture of compounds represented by formula (1) comprises 0 to 5 wt % of compounds in which m is an integer of 1 to 5 and n=0.

2. The mixture according to claim 1, wherein each Z is a phenyl group or naphthyl group.

3. The mixture according to claim 1, wherein formula (1) is one of the following formulas (1a) to (1d):

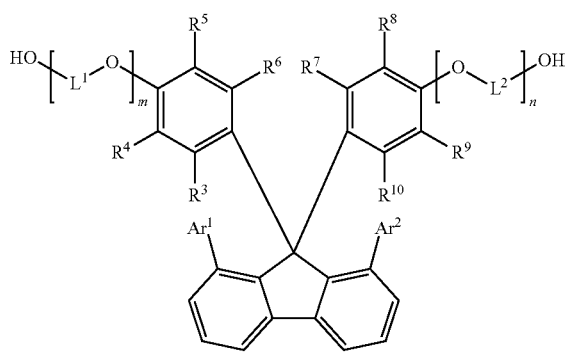

(1a)

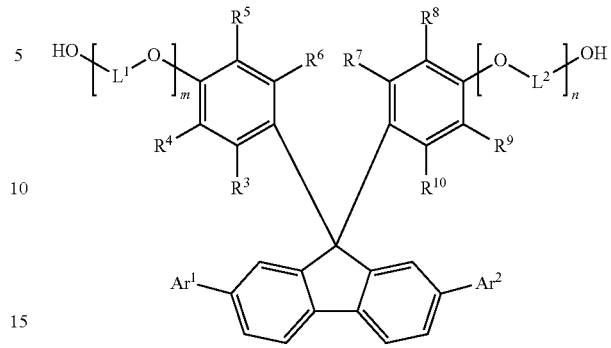

(1b)

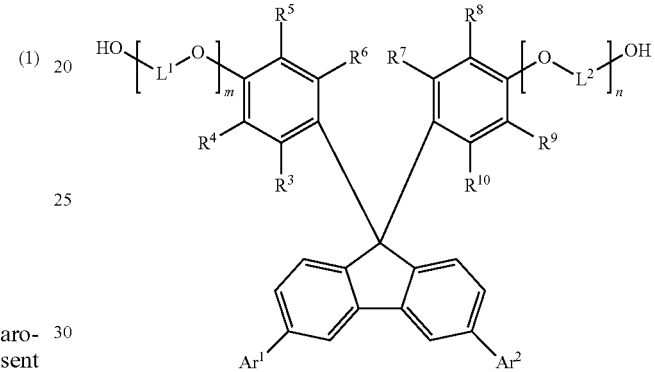

(1c)

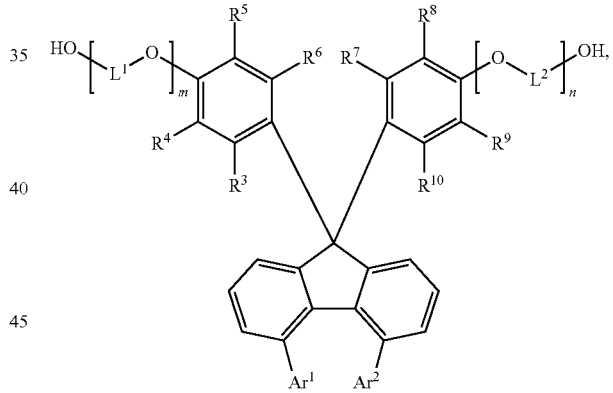

(1d)

wherein $R^3$ to $R^{10}$ each independently represent a hydrogen atom, a halogen atom or a hydrocarbon group of 1 to 12 carbon atoms optionally containing an aromatic group, and $Ar^1$ and $Ar^2$, $L^1$ and $L^2$, and m and n are the same as in formula (1) above.

4. The mixture according to claim 3, wherein formula (1) is formula (1b).

5. The mixture according to claim 1, wherein $Ar^1$ and $Ar^2$ in formula (1) are phenyl groups or naphthyl groups.

6. A method for producing a compound with a fluorene backbone represented by formula (1), which includes at least the following step 1 and step 2:

Step 1: A step in which a fluorenone represented by the following formula (3) and a boronic acid represented by the following formula (4) or (5) are reacted in a reaction solvent in the presence of a base and a palladium-based catalyst;

Step 2: A step in which the reaction product (6) produced in step 1 is reacted with an alcohol compound represented by the following formula (7) in a reaction solvent using an acid catalyst;

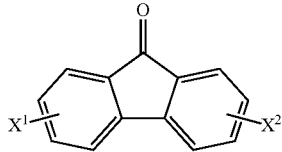
(3)

wherein $X^1$ is a substituent at position 1, position 2, position 3 or position 4, $X^2$ is a substituent at position 5, position 6, position 7 or position 8, and $X^1$ and $X^2$ are both halogen atoms,

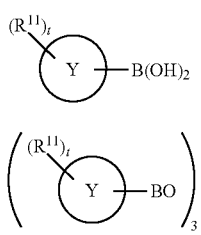
(4)

(5)

wherein Y is an aromatic group, $R^{11}$ is a hydrogen atom, an alkyl group, an alkenyl group, an alkoxy group or a halogen atom, l is 0, 1 or 2, and when l=2, the two $R^{11}$ groups may be the same or different,

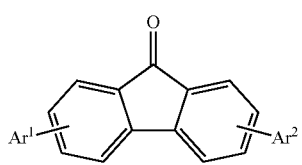
(6)

wherein $Ar^1$ and $Ar^2$ are the same as in formula (1),

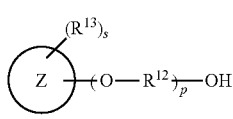
(7)

wherein z is the same as in formula (1), $R^{13}$ is a hydrogen or halogen atom or a hydrocarbon group of 1 to 12 carbon atoms optionally containing an aromatic group, s is independently an integer of 0 or greater, $R^{12}$ represents an alkylene group and p represents an integer of 0 or greater.

7. A method for producing a compound with a fluorene backbone represented by formula (1), which includes at least the following step (a) and step (b):
Step (a): A step in which a fluorenone represented by the following formula (3) and an alcohol compound represented by the following formula (7) are reacted in a reaction solvent in the presence of an acid catalyst;
Step (b): A step in which the reaction product (8) produced in step (a) is reacted with a boronic acid represented by the following formula (4) or (5) in a reaction solvent in the presence of a base and a palladium-based catalyst;

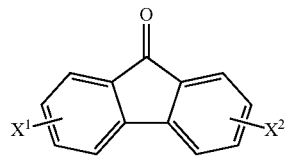
(3)

wherein $X^1$ is a substituent at position 1, position 2, position 3 or position 4, $X^2$ is a substituent at position 5, position 6, position 7 or position 8, and $X^1$ and $X^2$ are both halogen atoms,

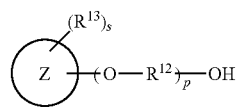
(7)

wherein Z is the same as in formula (1), $R^{13}$ is a hydrogen or halogen atom or a hydrocarbon group of 1 to 12 carbon atoms optionally containing an aromatic group, s is independently an integer of 0 or greater, $R^{12}$ represents an alkylene group and p represents an integer of 0 or greater,

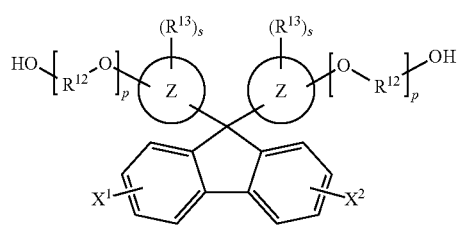
(8)

wherein $X^1$ and $X^2$ are the same as in formula (3), Z, $R^{13}$, s, $R^{12}$ and p are the same as in formula (7),

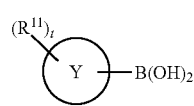
(4)

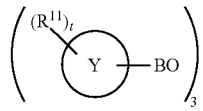
(5)

wherein Y is an aromatic group, $R^{11}$ is a hydrogen atom, an alkyl group, an alkenyl group, an alkoxy group or a halogen atom, l is 0, 1 or 2, and when l=2, the two $R^{11}$ groups may be the same or different.

8. The method for producing a compound with a fluorene backbone according to claim 6, wherein the compound represented by formula (3) is 2,7-dibromofluorenone.

9. The method for producing a compound with a fluorene backbone according to claim 6, wherein the compound represented by formula (4) is phenylboronic acid, 2-naphthaleneboronic acid or 1-naphthaleneboronic acid.

10. The method for producing a compound with a fluorene backbone according to claim 6, wherein the compound represented by formula (5) is phenylboronic anhydride, 2-naphthaleneboronic anhydride or 1-naphthaleneboronic anhydride.

11. The method for producing a compound with a fluorene backbone according to claim 6, wherein the compound represented by formula (6) is 2,7-diphenylfluorenone.

12. The method for producing a compound with a fluorene backbone according to claim 6, wherein the compound represented by formula (7) is 2-phenoxyethanol.

13. The method for producing a compound with a fluorene backbone according to claim 7, wherein the compound represented by formula (8) is 9,9-bis(2-hydroxyethoxy)phenyl)-2,7-dibromofluorene.

14. The method for producing a compound with a fluorene backbone according to claim 6, wherein the base used in step 1 is potassium carbonate and/or sodium carbonate.

15. The method for producing a compound with a fluorene backbone according to claim 6, wherein the catalyst used in step 1 is tetrakis(triphenylphosphine)palladium and/or palladium acetate.

16. The method for producing a compound with a fluorene backbone according to claim 6, wherein the reaction solvent used in step 1 is a mixed solvent of toluene and ethanol, or toluene.

17. The method for producing a compound with a fluorene backbone according to claim 6, wherein the acid catalyst used in step 2 is a heteropolyacid comprising phosphoric acid or silicic acid, and an oxo acid ion of at least one element selected from among vanadium, molybdenum and tungsten.

18. The method for producing a compound with a fluorene backbone according to claim 17, wherein the heteropolyacid is a heteropolyacid or heteropolyacid anhydride that has previously been subjected to dehydrating treatment.

19. The method for producing a compound with a fluorene backbone according to claim 6, wherein the reaction solvent used in step 2 is toluene.

20. A method of using a compound with a fluorene backbone according to claim 1 as a starting material for a thermoplastic resin.

21. The method for producing a compound with a fluorene backbone according to claim 7, wherein the compound represented by formula (3) is 2,7-dibromofluorenone.

22. The method for producing a compound with a fluorene backbone according to claim 7, wherein the compound represented by formula (4) is phenylboronic acid, 2-naphthaleneboronic acid or 1-naphthaleneboronic acid.

23. The method for producing a compound with a fluorene backbone according to claim 7, wherein the compound represented by formula (5) is phenylboronic anhydride, 2-naphthaleneboronic anhydride or 1-naphthaleneboronic anhydride.

24. The method for producing a compound with a fluorene backbone according to claim 7, wherein the compound represented by formula (7) is 2-phenoxyethanol.

25. The method for producing a compound with a fluorene backbone according to claim 7, wherein the base used in step (b) is potassium carbonate and/or sodium carbonate.

26. The method for producing a compound with a fluorene backbone according to claim 7, wherein the catalyst used in step (b) is tetrakis(triphenylphosphine)palladium and/or palladium acetate.

27. The method for producing a compound with a fluorene backbone according to claim 7, wherein the reaction solvent used in step (b) is a mixed solvent of toluene and ethanol, or toluene.

28. The method for producing a compound with a fluorene backbone according to claim 7, wherein the acid catalyst used in step (a) is a heteropolyacid comprising phosphoric acid or silicic acid, and an oxo acid ion of at least one element selected from among vanadium, molybdenum and tungsten.

29. The method for producing a compound with a fluorene backbone according to claim 28, wherein the heteropolyacid is a heteropolyacid or heteropolyacid anhydride that has previously been subjected to dehydrating treatment.

30. The method for producing a compound with a fluorene backbone according to claim 7, wherein the reaction solvent used in step (a) is toluene.

* * * * *